(12) United States Patent
Cooks et al.

(10) Patent No.: US 10,079,140 B2
(45) Date of Patent: Sep. 18, 2018

(54) SAMPLE ANALYSIS SYSTEMS AND METHODS OF USE THEREOF

(71) Applicant: Purdue Research Foundation, West Lafayette, IN (US)

(72) Inventors: Robert Graham Cooks, West Lafayette, IN (US); Zane Baird, West Lafayette, IN (US); Pu Wei, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/645,000

(22) Filed: Jul. 10, 2017

(65) Prior Publication Data

US 2018/0033603 A1    Feb. 1, 2018

Related U.S. Application Data

(63) Continuation of application No. 15/317,801, filed as application No. PCT/US2015/035926 on Jun. 16, 2015, now Pat. No. 9,704,700.

(60) Provisional application No. 62/074,938, filed on Nov. 4, 2014, provisional application No. 62/012,643, filed on Jun. 16, 2014.

(51) Int. Cl.
*H01J 49/24* (2006.01)
*H01J 49/06* (2006.01)
*H01J 49/14* (2006.01)
*H01J 49/00* (2006.01)

(52) U.S. Cl.
CPC .......... *H01J 49/24* (2013.01); *H01J 49/0013* (2013.01); *H01J 49/061* (2013.01); *H01J 49/142* (2013.01)

(58) Field of Classification Search
USPC ................ 250/281–284, 286, 288, 289, 292
See application file for complete search history.

(56) References Cited

U.S. PATENT DOCUMENTS

| | | | |
|---|---|---|---|
| 6,972,407 B2 | 12/2005 | Miller et al. | |
| 7,119,328 B2 * | 10/2006 | Kaufman | G01N 27/624 250/281 |
| 7,145,133 B2 | 12/2006 | Thomson | |
| 7,335,897 B2 | 2/2008 | Takats et al. | |
| 7,361,311 B2 | 4/2008 | Cooks et al. | |
| 7,977,629 B2 | 7/2011 | McEwen et al. | |

(Continued)

FOREIGN PATENT DOCUMENTS

| | | |
|---|---|---|
| WO | 2009/102766 A1 | 8/2009 |
| WO | 2010/127059 A1 | 11/2010 |
| WO | 2013/184320 A1 | 12/2013 |

OTHER PUBLICATIONS

Aebersold and Mann, Nature, 2003, 422, 198-207.

(Continued)

*Primary Examiner* — Bernard Souw
(74) *Attorney, Agent, or Firm* — Brown Rudnick LLP; Adam M. Schoen

(57) ABSTRACT

The invention generally relates to sample analysis systems and methods of use thereof. In certain aspects, the invention provides a system for analyzing a sample that includes an ion generator configured to generate ions from a sample. The system additionally includes an ion separator configured to separate at or above atmospheric pressure the ions received from the ion generator without use of laminar flowing gas, and a detector that receives and detects the separated ions.

19 Claims, 20 Drawing Sheets

(56) References Cited

U.S. PATENT DOCUMENTS

| | | | |
|---|---|---|---|
| 8,294,088 B2* | 10/2012 | Pringle | H01J 47/02 250/283 |
| 8,410,431 B2 | 4/2013 | Ouyang et al. | |
| 8,592,756 B2* | 11/2013 | Ouyang | H01J 49/0404 250/281 |
| 8,686,351 B2* | 4/2014 | Ouyang | H01J 49/0404 250/281 |
| 8,803,085 B2* | 8/2014 | Ouyang | H01J 49/0404 250/281 |
| 8,859,956 B2 | 10/2014 | Ouyang et al. | |
| 8,963,079 B2* | 2/2015 | Ouyang | H01J 49/0404 250/281 |
| 9,024,254 B2* | 5/2015 | Cooks | A61B 10/0045 250/288 |
| 9,159,540 B2* | 10/2015 | Ouyang | H01J 49/0404 |
| 9,184,038 B2* | 11/2015 | Cooks | H01J 49/067 |
| 9,484,195 B2* | 11/2016 | Ouyang | H01J 49/0404 |
| 9,538,945 B2* | 1/2017 | Cooks | A61B 10/0045 |
| 9,548,192 B2* | 1/2017 | Cooks | H01J 49/067 |
| 9,704,700 B2* | 7/2017 | Cooks | H01J 49/061 |
| 2011/0042560 A1 | 2/2011 | Ouyang et al. | |
| 2015/0136964 A1 | 5/2015 | Cooks et al. | |

OTHER PUBLICATIONS

Appelhans and Dahl, International Journal of Mass Spectrometry, 2005, 244, 1-14.
Badu-Tawiah, et al., J. Am. Soc. Mass Spectrom., 2012, 23, 1077-1084.
Badu-Tawiah, et al., J. Am. Soc. Mass Spectrom., 2012, 23, 842-849.
Cech and Enke, Mass Spectrometry Reviews, 2001, 20, 362-387.
Chen, et al., Journal of the American Chemical Society, 2007, 129, 5880-5886.
Cody et al., Anal. Chem., 77:2297-2302, 2005.
Cooks, et al., International Journal of Mass Spectrometry.
Cyriac, et al., Chemical Reviews, 2012, 112, 5356-5411.
Eberlin, Mass Spectrometry Reviews, 1997, 16, 113-144.
Fenn et al., Science 246 (4926): 64-71, 1989.
Fico et al., Anal. Chem., 2007, 79, 8076-8082.
Fu, et al., International Journal of Mass Spectrometry, 2009, 282, 77-84.
Gao et al., Anal. Chem. 80:7198-7205, 2008.
Gao et al., Z. Anal. Chem. 2006, 78, 5994-6002.
Gibson, et al., Additive Manufacturing Technologies, Springer US, 2010, pp. 160-186.
Hadjar, et al., Analytical Chemistry, 2007, 79, 6566-6574.
Ho et al., Clin Biochem Rev 24 (1): 3-12, 2003.
Hou et al., Anal. Chem., 83:1857-1861, 2011.
IPRP issued Dec. 20, 2016 in counterpart PCT Application No. PCT/US2015/035926.
Jennings, Journal of Aerosol Science, 1988, 19, 159-166.
Johnson, et al., Annual Review of Analytical Chemistry, 2011, 4, 83-104.
Karas et al., Journal of Analytical Chemistry, 366(6-7):669-676.
Kogelschatz, Plasma Chemistry and Plasma Processing, 23:1-46, 2003.
Li, et al., Angewandte Chemie International Edition, 2014, 53, 3147-3150.
Monge, et al., Chemical Reviews, 2013, 113, 2269-2308.
Mulligan et al., Chem.Com., 2006, 1709-1711.
Ouyang and Cooks, Annual Review of Analytical Chemistry, 2009, 2, 187-214.
Ouyang et al., Anal. Chem., 2009, 81, 2421-2425.
Parkins, Physics Today, 2005, 58.
Sanders et al., Euro. J. Mass Spectrom., 2009, 16, 11-20.
Search Report and Written Opinion dated Sep. 8, 2015 in PCT/US2015/035926.
Partial Search Report dated Feb. 28, 2018 in PCT/US2015/035926.
Shiea et al., J. Rapid Communications in Mass Spectrometry, 19:3701-3704, 2005.
Sokol et al., Int. J. Mass Spectrom., 2011, 306, 187-195.
Takats et al., Science, 306:471-473, 2004.
Wang et al., "Spatial Distribution Measurement of Ions Surrounding an Alpha Source using a New Micro-ionization Chamber," 2005, Journal of Nuclear Science and Technology, vol. 42, No. 12.
Xu et al., JALA, 2010, 15, 433-439.

* cited by examiner

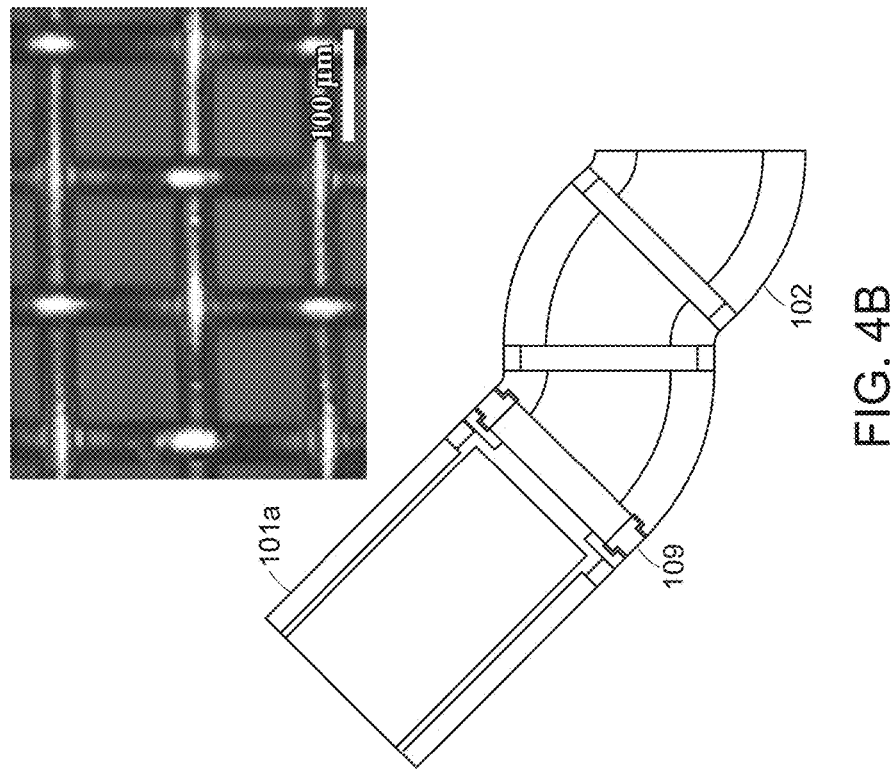
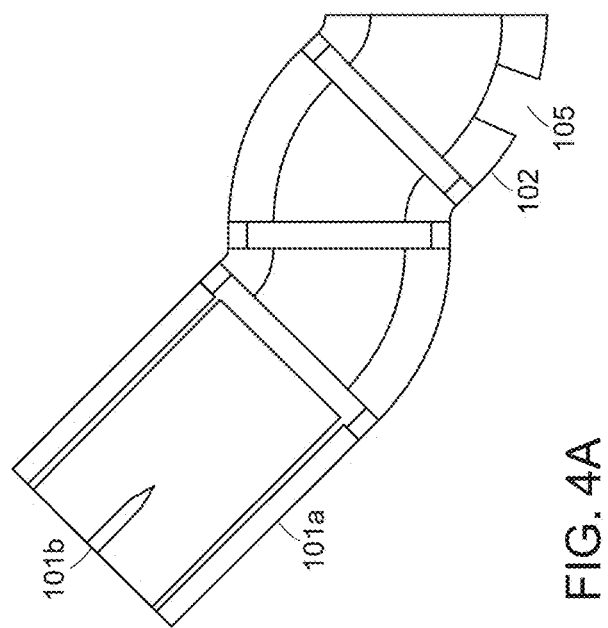
FIG. 4B
FIG. 4A

SAMPLE ANALYSIS SYSTEMS AND METHODS OF USE THEREOF

RELATED APPLICATIONS

The present application is a continuation of U.S. nonprovisional application Ser. No. 15/317,801, filed Dec. 6, 2016, which is a 35 U.S.C. § 371 national phase application of PCT/US15/35932, filed Jun. 16, 2015, which claims the benefit of and priority to each of U.S. provisional application Ser. No. 62/074,938, filed Nov. 4, 2014 and U.S. provisional application Ser. No. 62/012,643, filed Jun. 16, 2014, the content of each of which is incorporated by reference herein in its entirety.

GOVERNMENT SUPPORT

This invention was made with government support under CHE1307264 awarded by the National Science Foundation. The government has certain rights in the invention.

FIELD OF THE INVENTION

The invention generally relates to sample analysis systems and methods of use thereof.

BACKGROUND

Mass spectrometry (MS) is a very sensitive analytical method and one of the most widely used scientific tools with applications ranging from complex mixture analysis, to molecular biology and even large-scale purification and materials preparation. A mass spectrometer works by using magnetic and electric fields to exert forces on charged particles (ions) in a vacuum. Typically an ionization source is used to ionize an analyte at atmospheric pressure or inside a vacuum chamber before the ions are transferred to a vacuum environment of a mass spectrometer where the ions are focused, separated, and mass analyzed.

One challenge faced in all applications that use mass spectrometers is the low pressure environment required for analysis. Specifically, transfer, focusing and analysis of produced ions must be done under vacuum. Accordingly, MS analysis requires expensive vacuum pumps and manifolds to maintain a mass spectrometer under constant vacuum. Additionally, as vacuum pumps are cumbersome both physically and electrically, this also presents a challenge in the miniaturization of MS systems and their practical use due to the size and power requirements of commercially available MS platforms.

SUMMARY

The invention provides sample analysis systems that are configured to analyze ions at or above atmospheric pressure and without the use of laminar gas flow. Particularly, systems of the invention perform ion generation, ion transfer/focusing, gas-phase ion/molecule reactions, ion separation, and subsequent ion detection all in the ambient environment.

In certain aspects, the invention provides systems for analyzing a sample that include an ion generator configured to generate ions from a sample. The systems of the invention additionally include an ion separator configured to separate at or above atmospheric pressure the ions received from the ion generator without use of laminar flowing gas, and a detector that receives and detects the separated ions.

In certain embodiments, the ion generator includes an ionization source, and an ion injector configured to interface with the ionization source such that ions produced by the ionization source are received by the ion injector. Typically, although not required, the ionization source is out-of-line with the detector. The ion generator may be maintained at or above atmospheric pressure. However, in certain embodiments, the ion generator may be maintained below atmospheric pressure. Numerous configurations can exist for an ion injector. In certain embodiments, the ion injector includes a cavity and one or more wire meshes that receive the ions produced by the ionization source.

In certain embodiments, the ion separator includes a chamber and a plurality of electrodes that are configured such that upon application of voltage to the electrodes, ions received from the ion injector are separated as they travel through the chamber. In certain embodiments, the plurality of electrodes are three curved electrodes. Each of the three curved electrodes may be separated from each other by a non-conductive spacer. In certain embodiments, at least one of the three curved electrodes includes an opening through which a probe may be inserted.

The detector may be a mass spectrometer or a miniature mass spectrometer. Alternatively, another type of ion detector may be used, such as a pixelated charge collection detector (IONCCD).

Other aspects of the invention provide methods for analyzing a sample. Those methods may involve generating ions from a sample at or above atmospheric pressure, separating the ions at or above atmospheric pressure without use of laminar flowing gas, and detecting the separated ions, thereby analyzing the sample. The detecting step may be at or above atmospheric pressure. In other embodiments, the detecting step is below atmospheric pressure. In certain embodiments, detecting includes receiving the ions into a mass spectrometer or a miniature mass spectrometer.

In certain embodiments, the separating step includes transferring the ions into an ion separator that includes a chamber and a plurality of electrodes that are configured such that upon application of voltage to the electrodes, the ions are separated as they travel through the chamber. The plurality of electrodes may be three curved electrodes. Each of the three curved electrodes may be separated from each other by non-conductive spacer.

Other aspects of the invention provide methods for analyzing a reaction product. The methods involve generating ions at or above atmospheric pressure, separating the ions at or above atmospheric pressure without use of laminar flowing gas, introducing neutral molecules to the separated ions, reacting a portion of the separated ions with the neutral molecules to produce a reaction product, and detecting the reaction product.

Another aspect of the invention provides a method for collecting ions of an analyte of a sample that involves obtaining a sample, generating ions of an analyte from the sample, separating the ions at or above atmospheric pressure without the use of laminar gas flow, and collecting the separated ions, such as by depositing them at discrete locations on a surface.

Systems and methods of the invention can be used with any type of sample, such as organic or non-organic, biological or non-biological, etc. In certain embodiments, the sample is derived from a biological tissue or is a biological fluid, such as blood, urine, saliva, or spinal cord fluid. The sample may include an analyte of interest to be analyzed. That analyte can be native to the sample or may have been introduced into the sample. Exemplary analytes include therapeutic drugs, drugs of abuse and other biomarkers. The examples herein show analysis of therapeutic drugs, drugs of abuse and other compounds. In certain embodiments, systems and methods of the invention can be used for direct analysis of biofluid samples or liquid samples. That is, systems and methods of the invention can be used without performing an sample preparation or purification steps.

BRIEF DESCRIPTION OF THE DRAWINGS

FIGS. 4A-B show another embodiment of an ion injector. FIG. 4A shows the ion injector with the ionization source and FIG. 4B shows the ion injector without the ionization source.

FIG. 14A is a diagram of a setup showing axis of cylindrical symmetry and an electrode with filaments connecting a central disc electrode to an outer cylinder. FIG. 14B is an example of a 2 dimensional reconstruction of ion intensity at the deposition surface observed when using the annular focusing electrode, which is shown in FIG. 14C. FIG. 14C shows the annular focusing electrode.

DETAILED DESCRIPTION

The invention generally relates to sample analysis systems and methods of use thereof. Systems of the invention are configured to separate ions of different mass/charge ratio in air without the use of laminar gas flow. Accordingly, systems of the invention provide a single integrated instrument to perform ionization in air, ion transport from an ionization source to a detector in air while accomplishing ion focusing and ion detection in air. In that manner, systems and methods of the invention transfer the elements of mass spectrometry to air.

As shown herein, a system composed of small plastic electrodes was fabricated and used to demonstrate several cases of gas-phase ion manipulation in the open air. These manipulations highlight some of the possible uses of 3D printed plastic electrodes for focusing and transfer of ions to a mass spectrometer, including cases in which an ion/molecule reaction is performed within the electrodes at atmospheric pressure. The separation of ions demonstrated in the simple, low-cost system demonstrates that a device may be constructed in which ions may be purified through soft-landing or directly analyzed, all without the constraints of a vacuum system or well defined gas flow. Moreover, the detection and two dimensional profiling of the ion beam under ambient conditions, combined with the low cost of electrode production, paves the way for distinct surface patterning with unorthodox electrode geometries.

Figure 1A:
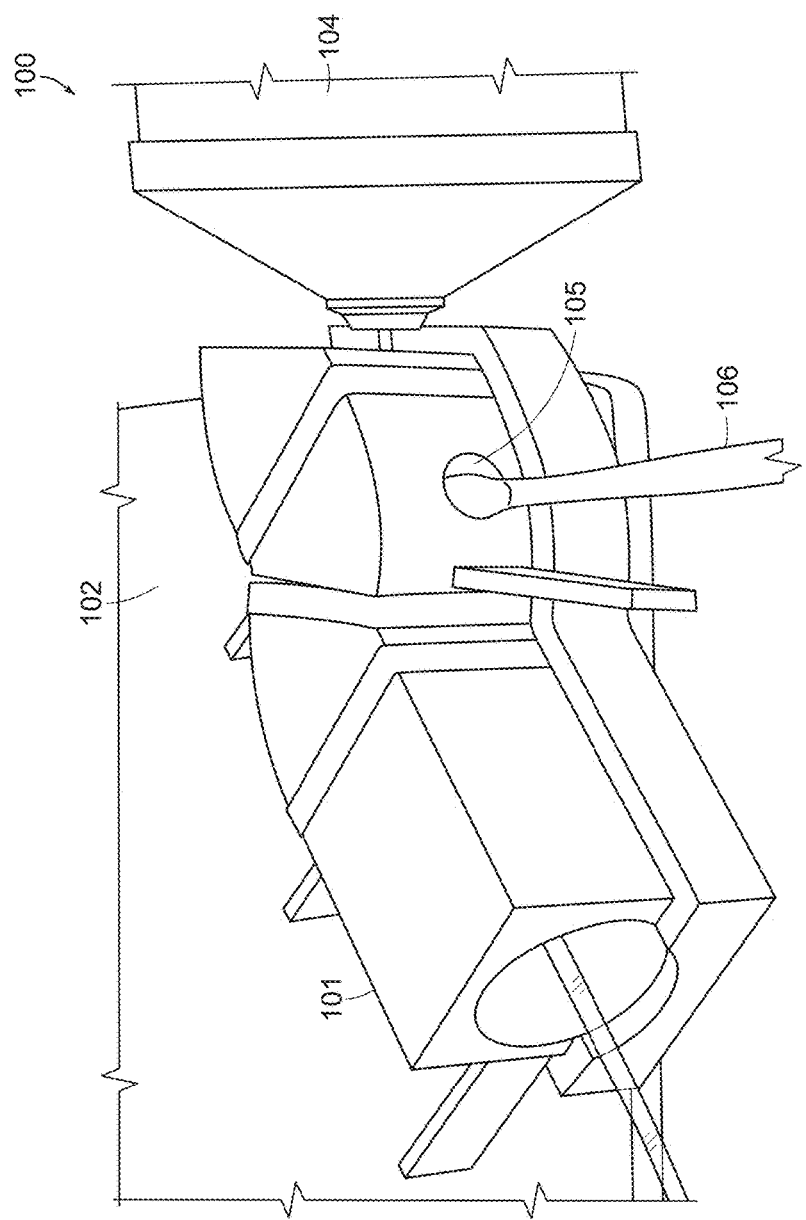
FIGS. 1A and 1B show embodiments of a system of the invention.
Figure 1B:
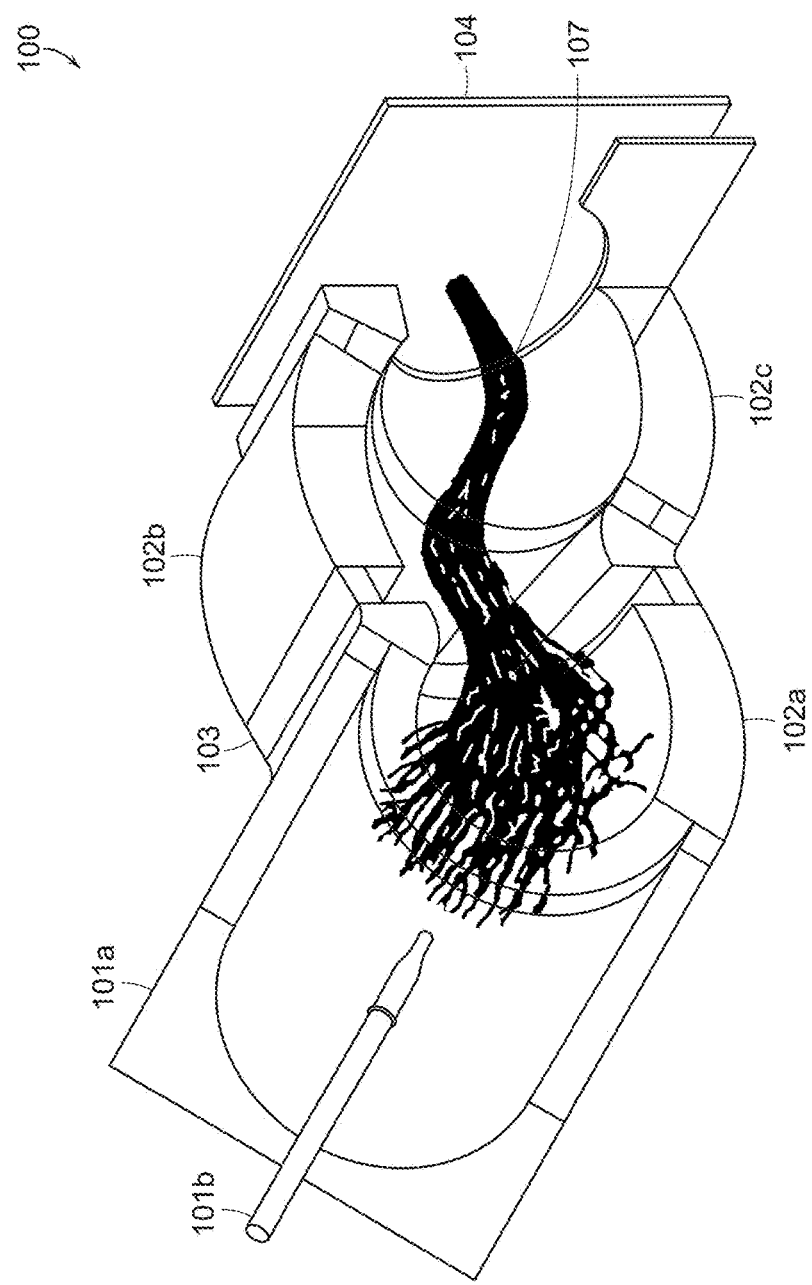

FIGS. 1A and 1B show embodiments of systems of the invention. In certain aspects, the invention provides a system 100 for analyzing a sample that includes an ion generator 101 configured to generate ions 105 from a sample. The system additionally includes an ion separator 102 configured to separate at or above atmospheric pressure the ions 105 received from the ion generator 101 without use of laminar flowing gas, and a detector 104 that receives and detects the separated ions 105. In certain embodiments, the system is configured to operate in an ambient or above ambient environment, and there is no need for a gas or gas inlet to provide turbulent or laminar flow through the apparatus.

The ion generator 101 includes an ion injector 101a and ionization source 101b. FIGS. 1A, 1B and FIGS. 4A-B show exemplary ion injectors 101a. Each ion injector 101a shown in these figures includes an open hollow cylindrical electrode that interfaces with ionization source 101b (FIG. 4A). Because the ion injector 101a is open, it can be held at or above atmospheric pressure. In certain embodiments, within the cylindrical electrode are two metal meshes 109 (FIG. 4B). The metal meshes 109 are configured such that they are separated by about 3 mm. A floated high voltage pulse (2,530 V high, 2,480 V low) was applied to the mesh directly after the hollow cylindrical electrode with the second of the two meshes held flush to an opening of the ion separator 102 to facilitate electrical contact to the ion separator 102. Such a set-up allowed for controlled ion injection to the ion separator 102. An exemplary mode operation involved a pulse width of 50 ms with a repetition rate of 1 Hz for ion injection.

Figure 2A:
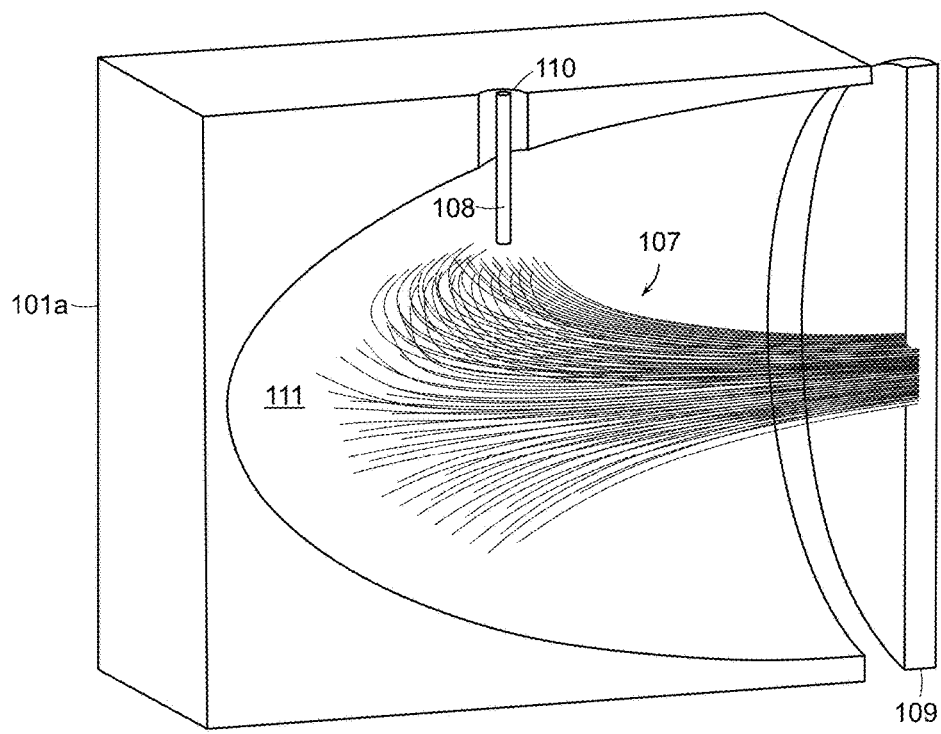
FIG. 2A shows an embodiment of an ion injector.

Another exemplary ion injector 101a is described for example in U.S. patent application Ser. No. 14/391,867, the content of which is incorporated by reference herein in its entirety. In these embodiments, the ion injector 101 includes an electrode having a cavity 111 (FIG. 2A). There is an at least one inlet 110 within the cavity 101a configured to operatively couple with an ionization source 101b, such that discharge generated by the source (e.g., charged microdroplets) is injected into the cavity 111, and is focused to an outlet. As shown in FIG. 1B, the ionization source 101b is out-of-line with detector 104, which greatly reduces neutral transmission. The cavity 111 is shaped such that upon application of voltage to the electrode, ions within the cavity 111 are focused and directed to the outlet, which is positioned such that a proximal end of the outlet receives the focused ions and a distal end of the outlet is open to ambient pressure. The term ion includes charged microdroplets. Generally, the outlet is grounded.

The cavity 111 can be any shape that allows for the focusing of ions. In certain embodiments, the cavity 111 has an ellipsoidal shape. In this embodiment, the cavity 111 is arranged such that the narrowest portion of the ellipsoid is positioned farthest from the outlet and the widest portion of the ellipsoid is positioned closest to the outlet. In other embodiments, the cavity is a hollow half-ellipsoidal cavity, i.e., the cavity 111 is open to the air. In other embodiments, the cavity 111 is domed shaped and connected to the outlet such that the cavity 111 seals to the outlet. In this manner, the cavity 111 may be pressurized. In other embodiments, the outlet is not connected to the cavity 111, rather it is in close proximity to the opening of the elliptical cavity 111 to produce electrical fields that facilitate the focusing of the ions in the cavity 111 generated by the ionization source 101b.

Ion injector 101a may further include a gas inlet in order to produce a turbulent flow within the cavity 111. The gas flow both enhances the desolvation of charged microdroplets to produce ions for analysis and can assist in focusing the ions with appropriate flow fields. Ion injector 101a may further include a plurality of ring electrodes positioned within an interior portion of the cavity 111 such that they are aligned with the outlet, in which the electrodes are arranged in order of decreasing inner diameter with respect to the outlet.

The ionization source 101b may be any ambient ionization source. Exemplary mass spectrometry techniques that utilize direct ambient ionization/sampling methods including PAPERSPRAY (ion generation using wetted porous material; Purdue Research Foundation, U.S. Pat. No. 8,859, 956), desorption electrospray ionization (DESI; Takats et al., Science, 306:471-473, 2004 and U.S. Pat. No. 7,335,897); direct analysis in real time (DART; Cody et al., Anal. Chem., 77:2297-2302, 2005); Atmospheric Pressure Dielectric Barrier Discharge Ionization (DBDI; Kogelschatz, Plasma Chemistry and Plasma Processing, 23:1-46, 2003, and PCT international publication number WO 2009/102766), and electrospray-assisted laser desorption/ionization (ELDI; Shiea et al., J. Rapid Communications in Mass Spectrometry, 19:3701-3704, 2005). The content of each of these references in incorporated by reference herein its entirety. In other embodiments, the probe operates by electrospray ionization (Fenn et al., Science 246 (4926): 64-71, 1989; and Ho et al., Clin Biochem Rev 24 (1): 3-12, 2003) or nano-electrospray ionization (Karas et al., Journal of Analytical Chemistry, 366(6-7):669-676, 2000). The content of each of these references in incorporated by reference herein its entirety. In other embodiments, the probe is a paper spray probe (international patent application number PCT/US10/32881). In other embodiments, the probe is a low temperature plasma probe. Such probes are described in U.S. patent application Ser. No. 12/863,801, the content of which is incorporated by reference herein in its entirety.

Exemplary sources include an electrospray probe or a nano-electrospray probe. In certain embodiments, the inlet 110 of the ion injector 101a is configured to receive an electrospray capillary such that the spray (charged microdroplets) produced by the capillary is directly injected into the cavity 111 of the electrode. This is illustrated in FIG. 2A in which an electrospray capillary 108 is inserted within ion injector 101a and into cavity 111. In other embodiments, the ion injector 101a is configured to couple with a long distance transfer line such that spray produced from ionization source 101b a distance from the ion injector 101a can still be directed into the cavity 111 for focusing of ions. Long distance transfer of charged microdroplets and/or ions and devices for accomplishing such long distance transfer are shown for example in U.S. Pat. No. 8,410,431, the content of which is incorporated by reference herein in its entirety.

Figure 2B:
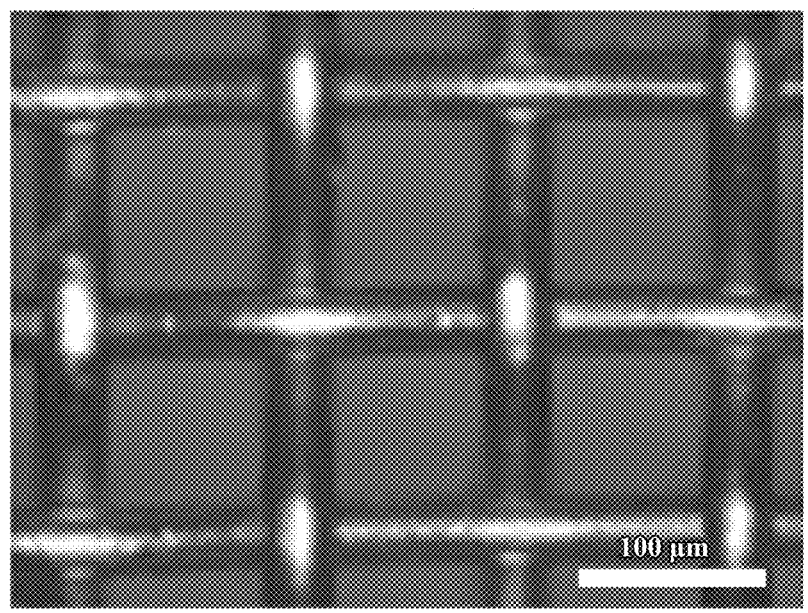
FIG. 2B shows an exemplary metal mesh.

Ion injector 101a may also include metal meshes 109 (FIGS. 2A and 2B). The metal meshes 109 are configured such that they are separated by about 3 mm. A floated high voltage pulse (2,530 V high, 2,480 V low) was applied to the mesh directly after the cavity 111 with the second of the two meshes held flush to an opening of the ion separator 102 to facilitate electrical contact to the ion separator 102. Such a set-up allowed for controlled ion injection to the ion separator 102. An exemplary mode operation involved a pulse width of 50 ms with a repetition rate of 1 Hz for ion injection.

While not being limited by any particular theory or mechanism of action, an explanation of ion focusing is provided. For a given geometry, the potential can be expressed as:

$$V(x,y,z) \text{ or } V(r,\theta,z).$$

Due to a cylindrical symmetry ($V_\theta$=const. for all the arbitrary x,z), the potential can be reduced to a 2-dimensional coordinate system V(x, z). To determine whether ions are concentrated or not, two conditions must be matched.

Figure 3:
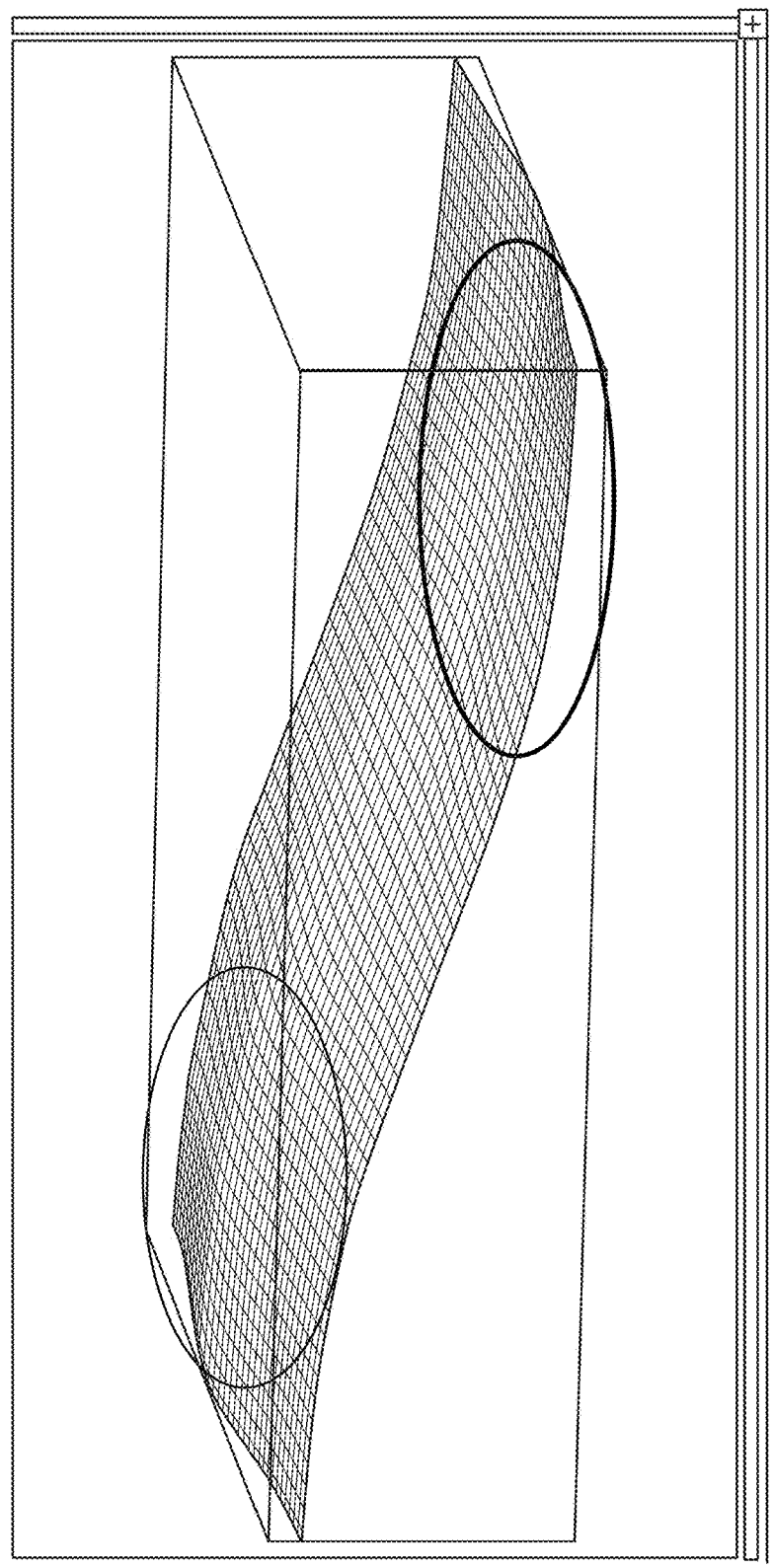
FIG. 3 is the potential view of an elliptical geometry.

(i) $E_z(x) = \dfrac{\partial V}{\partial z} = 0$ for all $x$ (ii) $\begin{cases} \dfrac{\partial^2 V}{\partial z^2} > 0 \text{ then ions are focusing} & (1) \\ \dfrac{\partial^2 V}{\partial z^2} = 0 \text{ then ions run into the focusing limit} & (2) \\ \dfrac{\partial^2 V}{\partial z^2} < 0 \text{ then ions are defocusing} & (3) \end{cases}$ These three cases can be easily determined by the potential graph as shown in FIG. 3. FIG. 3 is the potential view of an elliptical geometry, the circle on the left indicates case (3), the circle on the right indicates case (1), and case (2) must be a point between the two circles. For that analysis, it is believed that all cavity-like geometries are able to focus ions to a certain area.

The focused ions from the ion generator 101 are transferred to the ion separator 102. The ion separator includes curved electrodes 102a-c, which are separated from each other by non-conductive spacers 103. The ion separator 102 operates without the use of laminar gas flow or gas flow of any type. Rather, the curvature of the electrodes produces a curved ion path and the curved electrodes are held at certain voltages as the ions are received from the ion generator 101 and injected into the ion separator 102. In that manner, as ions are injected into the ion separator 102, they move along the charged curved path. The voltage acts on the ions as they travel the curved path through the ion separator 102, causing the ions to separate based upon their mass to charge ratio.

Each of curved electrodes 102a-c may have a separate and distinct voltage from its neighboring electrode and from the ion generator 101. The voltage for each of curved electrodes 102a-c and the ion generator 101 may be controlled by its own source or the voltage may be provided by one source in combination with a series of resistors to form a voltage divider. The design of the curved electrodes was based on simulations of ion trajectories with the device, using commercially available software (e.g., SIMION 8.0; Scientific Instrument Services), which is described in the examples below. Briefly, 3D models of the electrode assemblies were constructed and converted to stereolithography (STL) format. STL files were then converted to potential arrays using the SL toolbox of SIMION 8.0. Simulations were carried out using the SDS algorithm with an arithmetic distribution of ions from 50-800 m/z (n=5). Electrodes were produced via fused deposition modeling (FDM) on a RepRap style 3D printer (Prusa i3) using 1.75 mm conductive ABS filament and printed at 0.2 mm layer height. 2D images of the ion swarm at the deposition surface were taken by scanning an IonCCD™ (OI Analytical) detector across the exit region of the electrode assembly and reconstructed based on scan rate. Ion separation was achieved by applying a floated HV pulse on the source electrode.

The skilled artisan will appreciate that the design of the electrodes and the configuration of the system can be modified by performing other simulations of ion trajectories using the software mentioned herein. The skilled artisan will also recognize that the number of electrodes and spacers for the ion separator is merely exemplary, and systems of the invention can include fewer or more curved electrodes and spacers. The voltage may be tuned or modified to affect the amount of ions introduced into the ion injection region, to modify the ion beam, or to control the movement of the injected ions through the apparatus whether that be to hold or release the ions from the injection region. Electrodes may be generated from any material that is able to hold a voltage, and is not limited to size or shape. The dimensions of the apparatus may be further optimized by modifications to the geometry and dimensions. For instance, a series of electrodes with decreasing diameters may be used to concentrate ions to a smaller spot size at the exit electrode or thinner and more numerous electrodes (i.e. six or more) could be used to create a more uniform electric field within the device to optimize the transmission of ions. It should also be noted that the production of electrodes achieved by fused deposition modeling (FDM) allows for unconventional geometries. Additionally, with a multi-nozzle FDM printer it will be possible to construct a device consisting of multiple electrodes and spacers that is a single solid piece. Any 3D printing device and available software may be useful to generate the apparatus.

The separated ions 107 are transferred from the ion separator 102 to a detector 104. Any detector that can detect ions can be used with systems and methods of the invention. The detector may be maintained at any pressure. For example, the detector may be maintained at atmospheric pressure. In other embodiments, the detector is maintained below or above atmospheric pressure. As shown in FIG. 1A, an exemplary ion detector 104 may be a mass spectrometer or a miniature mass spectrometer. In fact, any type of mass spectrometer known in the art can be used with systems and methods of the invention. For example, the mass spectrometer can be a standard bench-top mass spectrometer. In other embodiments, the mass spectrometer is a miniature mass spectrometer. An exemplary miniature mass spectrometer is described, for example in Gao et al. (Z. Anal. Chem. 2006, 78, 5994-6002), the content of which is incorporated by reference herein in its entirety In comparison with the pumping system used for lab-scale instruments with thousands watts of power, miniature mass spectrometers generally have smaller pumping systems, such as a 18 W pumping system with only a 5 L/min (0.3 m3/hr) diaphragm pump and a 11 L/s turbo pump for the system described in Gao et al. Other exemplary miniature mass spectrometers are described for example in Gao et al. (Anal. Chem., 80:7198-7205, 2008), Hou et al. (Anal. Chem., 83:1857-1861, 2011), and Sokol et al. (Int. J. Mass Spectrom., 2011, 306, 187-195), the content of each of which is incorporated herein by reference in its entirety. Miniature mass spectrometers are also described, for example in Xu et al. (JALA, 2010, 15, 433-439); Ouyang et al. (Anal. Chem., 2009, 81, 2421-2425); Ouyang et al. (Ann. Rev. Anal. Chem., 2009, 2, 187-214); Sanders et al. (Euro. J. Mass Spectrom., 2009, 16, 11-20); Gao et al. (Anal. Chem., 2006, 78(17), 5994-6002); Mulligan et al. (Chem. Com., 2006, 1709-1711); and Fico et al. (Anal. Chem., 2007, 79, 8076-8082), the content of each of which is incorporated herein by reference in its entirety.

In other embodiments, such as shown in FIG. 1B, the detector 104 is a detector that can detect ions at atmospheric pressure. Such an exemplary detector is an IONCCD detector (atmospheric pressure ion detector, commercially available from OI Analytical). This exemplary detector is a 2126-pixel CCD array detector that has been modified to directly detect positively and negatively charged particles. Each pixel is 21-μm wide and 1.5-mm high with a 3-μm insulating gap. The result is a 51 mm long array with 24-μm pitch and 88% effective area. The detector and its operation is further described in IonCCD 9-2013—Publication #3897, the content of which is incorporated by reference herein in its entirety.

In certain embodiments, the systems of the invention are configured for conducting ion/molecule reactions. To accomplish that, one or more of electrodes 102a-c have an opening through which a probe may be inserted (FIG. 1A and FIG. 4A). For example, FIG. 1A shows a configuration in which one of the electrodes of the ion separator 102 includes an opening 105 through which probe 106 can be inserted. Probe 106 includes one or more reactants that will interact with ions 107 as those ions pass through ion separator 102. A reaction product is produced that is detector by detector 104. The skilled artisan will appreciate that the system configuration shown in FIG. 1A is exemplary. In certain embodiments, more than open opening is used, for example, more than one of electrodes 102a-c include an opening. The opening can also be on any portion of electrodes 102a-c and can be located on any one of electrodes 102a-c. Additionally, the opening can be any size, and the size will typically be based on the size of the probe that needs to be inserted into the opening.

Systems and methods of the invention can be used with any type of sample, such as organic or non-organic, biological or non-biological, etc. In certain embodiments, the sample is derived from a biological tissue or is a biological fluid, such as blood, urine, saliva, or spinal cord fluid. The sample may include an analyte of interest to be analyzed. That analyte can be native to the sample or may have been introduced into the sample. Exemplary analytes include therapeutic drugs, drugs of abuse and other biomarkers. In certain embodiments, systems and methods of the invention can be used for direct analysis of biofluid samples or liquid samples. That is, systems and methods of the invention can be used without performing any sample preparation or purification steps.

Systems and methods of the invention are also useful for producing and separating ions in air that can be collected (soft landed) on surfaces for use as reagents for chemical reactions occurring at surfaces. Systems and methods for collecting ions are shown in Cooks, (U.S. Pat. No. 7,361, 311), the content of which is incorporated by reference herein in its entirety. In particular embodiments, systems and methods of the invention are coupled with nanoESI probes because nanoESI probes use a low flow rate such that molecular ions of low internal energy are produced, thus avoiding fragmentation.

Systems and methods of the invention allow for the capture of intact polyatomic ions at a condensed phase interface—and reactive ion/surface collisions. The surfaces can subsequently be analyzed. Surface characterization methods include keV energy ion sputtering (SIMS), temperature programmed desorption (TPD), and surface enhanced Raman spectroscopy (SERS). Systems and methods of the invention can be used to investigate any chemical system. Exemplary chemical systems that can be investigated using apparatuses of the invention include olefin epoxidation, transacylation, aza-Diels-Alder reactions and nitrogen fixation into alkanes.

Another use for the invention is for altering chemical functionalities at a surface. Ions and charged droplets impinging on a surface have been shown to increase the efficiency and rate of chemical reactions occurring at the surface (Abraham et al., Journal of the American Society of Mass Spectrometry, 2012, 23, 1077-1084; Abraham et al., Journal of the American Society of Mass Spectrometry, 2012, 23, 842-849; and Abraham et al., Angewandte Chemie International Edition, 2012, 51, 1-6). This, when coupled with ion separating with apparatuses and methods of the invention at or above atmospheric pressure, allows for embodiments in which ions are used to alter the chemical functionalities at a surface in a spatially resolved manner, all performed at atmospheric pressure. One example of such a case is the site-specific silylation of a glass surface via reactions of silylation agents (in charged droplets, or as free ions) with hydroxyl groups present on the glass to create hydrophobic areas. When combined with ambient ion separating, spatially controlled chemically specific surface modification can be achieved at atmospheric pressure. This capability is not limited to silylation chemistry, which serves simply as one example of the chemistry possible.

Collection of Ions

Systems and methods for collecting ions are shown in Cooks, (U.S. Pat. No. 7,361,311), the content of which is incorporated by reference herein in its entirety. Generally, the preparation of microchips arrays of molecules first involves the ionization of analyte molecules in the sample (solid or liquid). The molecules can be ionized by any method. The ions can then be separated and collected using systems and methods described herein.

To achieve this, a microchip or substrate is moved or scanned in the x-y directions and stopped at each spot location for a predetermined time to permit the deposit of a sufficient number of molecules to form a spot having a predetermined density. Alternatively, the gas phase ions can be directed electronically or magnetically to different spots on the surface of a stationary chip or substrate. The molecules are preferably deposited on the surface with preservation of their structure, that is, they are soft-landed. Two facts make it likely that dissociation or denaturation on landing can be avoided. Suitable surfaces for soft-landing are chemically inert surfaces that can efficiently remove vibrational energy during landing, but which will allow spectroscopic identification. Surfaces which promote neutralization, rehydration or having other special characteristics might also be used for protein soft-landing.

Generally, the surface for ion landing is located after the ion separator or alternatively after the detector. Without a detector, separated ions are landed directly onto a surface. When using a mass spectrometer as a detector, the high voltages on the conversion dynode and the multiplier are turned on and the ions are detected to allow the overall spectral qualities, signal-to-noise ratio and mass resolution over the full mass range to be examined. In the ion-landing mode, the voltages on the conversion dynode and the multiplier are turned off and the ions are allowed to pass through the hole in the detection assembly to reach the landing surface of the plate (such as a gold plate). The surface is grounded and the potential difference between the source and the surface is 0 volts.

An exemplary substrate for soft landing is a gold substrate (20 mm×50 mm, International Wafer Service). This substrate may consist of a Si wafer with 5 nm chromium adhesion layer and 200 nm of polycrystalline vapor deposited gold. Before it is used for ion landing, the substrate is cleaned with a mixture of $H_2SO_4$ and $H_2O_2$ in a ratio of 2:1, washed thoroughly with deionized water and absolute ethanol, and then dried at 150° C. A Teflon mask, 24 mm×71 mm with a hole of 8 mm diameter in the center, is used to cover the gold surface so that only a circular area with a diameter of 8 mm on the gold surface is exposed to the ion beam for ion soft-landing of each mass-selected ion beam. The Teflon mask is also cleaned with 1:1 MeOH:$H_2O$ (v/v) and dried at elevated temperature before use. The surface and the mask are fixed on a holder and the exposed surface area is aligned with the center of the ion optical axis.

Any period of time may be used for landing of the ions. Between each ion-landing, the Teflon mask is moved to expose a fresh surface area, and the surface holder is relocated to align the target area with the ion optical axis. After soft-landing, the Teflon mask is removed from the surface.

In another embodiment a linear ion trap can be used as a component of a soft-landing instrument. Ions travel through a heated capillary into a second chamber via ion guides in chambers of increasing vacuum. The ions are captured in the linear ion trap by applying suitable voltages to the electrodes and RF and DC voltages to the segments of the ion trap rods. The stored ions can be radially ejected for detection. Alternatively, the ion trap can be operated to eject the ions of selected mass through the ion guide, through a plate onto the microarray plate. The plate can be inserted through a mechanical gate valve system without venting the entire instrument.

The advantages of the linear quadrupole ion trap over a standard Paul ion trap include increased ion storage capacity and the ability to eject ions both axially and radially. Linear ion traps give unit resolution to at least 2000 Thomspon (Th) and have capabilities to isolate ions of a single mass/charge ratio and then perform subsequent excitation and dissociation in order to record a product ion MS/MS spectrum. Mass analysis will be performed using resonant waveform methods. The mass range of the linear trap (2000 Th or 4000 Th but adjustable to 20,000 Th) will allow mass analysis and soft-landing of most molecules of interest. In the soft-landing instrument described above the ions are introduced axially into the mass filter rods or ion trap rods. The ions can also be radially introduced into the linear ion trap.

The ions can be separated in time so that the ions arrive and land on the surface at different times. While this is being done the substrate is being moved to allow the separated ions to be deposited at different positions. The ions can be directed to different spots on a fixed surface by scanning electric or magnetic fields.

It is desirable that the structure of the analyte be maintained during the soft-landing process. On such strategy for maintaining the structure of the analyte upon deposition involves keeping the deposition energy low to avoid dissociation or transformation of the ions when they land. This needs to be done while at the same time minimizing the spot size. Another strategy is to mass select and soft-land an incompletely desolvated form of the ionized molecule. Extensive hydration is not necessary for molecules to keep their solution-phase properties in gas-phase. Hydrated molecular ions can be formed by electrospray and separated while still "wet" for soft-landing. The substrate surface can be a "wet" surface for soft-landing, this would include a surface with as little as one monolayer of water. Another strategy is to hydrate the molecule immediately after mass-separation and prior to soft-landing. One strategy is to deprotonate the mass-selected ions using ion/molecule or ion/ion reactions after separation but before soft-landing, to avoid undesired ion/surface reactions or protonate at a sacrificial derivatizing group which is subsequently lost.

Different surfaces are likely to be more or less well suited to successful soft-landing. For example, chemically inert surfaces which can efficiently remove vibrational energy during landing may be suitable. The properties of the surfaces will also determine what types of in situ spectroscopic identification are possible. The ions can be soft-landed directly onto substrates suitable for MALDI. Similarly, soft-landing onto SERS-active surfaces is possible.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

The Examples herein illustrate systems and methods in which ions are generated and manipulated in the ambient environment using polymeric electrodes produced with a consumer-grade 3D printer. The ability to focus, separate, react, and detect ions in the ambient environment is demonstrated and the data agree well with simulated ion behavior. This work demonstrates ion generation, ion transfer/focusing, gas-phase ion/molecule reactions, ion separation, and subsequent ion detection all in the ambient environment using plastic electrodes produced via rapid prototyping. In some Examples, the device is used to prepare ions for mass analysis in a mass spectrometer while in other cases it is used in a stand-alone fashion as a reactor/analysis system.

Example 1

Electrodes and Materials

Electrodes were printed at 200 µm layer height with an FDM 3D printer (Prusa i3v, Makerfarm) from 1.75 mm conductive ABS filament (Makergeeks). Machine code (g-code) generation for the printed part production was performed in Slic3r v1.1.6 with a 25% hexagonal infill. All nanoESI emitters were pulled from 1.5 mm OD, 1.1 mm ID borisilicate glass capillaries on a Sutter P-97 micropipette puller to a final tip diameter of 5 µm. Dimethyl methylphosphonate, tetradodecylammonium bromide, and tetrahexylammonium bromide were purchased from Fluka Analytical. Cyclohexylamine, and tetrabutylammonium bromide acquired from Eastman Chemical. HPLC grade acetonitrile and methanol were purchased from Sigma-Aldrich and Macron Fine Chemicals, respectively.

Example 2

Fundamentals of Ion Motion at Atmospheric Pressure and Simulation Environment

The simulation of gaseous ion trajectories has been used extensively in the development of ion optics for MS, IMS, electron microscopes (EM), and focused ion beam (FIB) systems. In the case of systems operating in high-vacuum (EM and FIB) the simulation environment is often simplified and assumed to be collision-free and ion motion is influenced purely by electric and magnetic fields; however, IMS and many MS systems operate in a pressure regime in which collisions cannot be neglected. SIMION 8.0 includes two collision models (HS1 and SDS) that can be incorporated for the treatment of these collisions. HS1 employs hard-sphere collision kinetics to compute the resulting ion trajectory change for ion-molecule collisions individually. This approach is not computationally feasible at atmospheric pressures as the mean free path in air at 25° C. is approximately 67 nm². Rather than treating individual collisions, the SDS algorithm uses a combined approach of diffusion and ion mobility to simulate ion motion in electric fields.

The motion of ions at atmospheric pressure is heavily influenced by the diffusion of ions in the medium, as well as by external forces exerted on the ions (electric fields, bulk gas flow, etc.). Diffusion can be expressed as:

$$J = D\nabla_n \qquad \text{Eq. 1}$$

where J, D, and $\nabla_n$ are the number of ions passing through an area normal to the gas flow, a proportionality constant, and the concentration gradient, respectively. In the SIMION-SDS algorithm, diffusion is simulated by imposing a random ion jump onto the ion trajectory. The radius of the jump is determined by an interpolation between collision statistics tables (selected based on the mass ratio of the ion to a background gas molecule) and scaled appropriately based on an expected number of collisions in the simulation time step.

When subjected to an electric field (E), the velocity of an ion in a gas with no bulk flow is determined by its mobility (K) in the buffer gas.

$$v = KE \quad \text{Eq. 2}$$

K is determined experimentally and is directly proportional to D and the charge (e) on the ion and inversely proportional to temperature (T) multiplied by the Boltzmann constant (k)[3].

$$K = \frac{eD}{kT} \quad \text{Eq. 3}$$

This is known as the Nernst-Townsend relation and holds for the cases in which ions are thermalized. The mobility can further be expressed as:

$$K = \frac{3e}{16N}\left(\frac{2\pi}{\mu kT}\right)^{1/2}\left(\frac{1}{Q_D}\right) \quad \text{Eq. 4}$$

Where N is the density of the neutral molecules, $\mu$ is the reduced mass of the collision pair, and $Q_D$ is the collisional cross section. Due to the range of working conditions used in IMS instruments, the mobility of an ion is often reported as the reduced mobility ($K_0$) which is corrected for 273 K and a pressure (P) of 760 Torr:

$$K_0 = K\left(\frac{273}{T}\right)\left(\frac{P}{760}\right) \quad \text{Eq. 5}$$

At each time step within a SIMION-SDS simulation, the velocity of an ion is subjected to the effects of gas flow and the applied electric field, in the form of mobility (Eq. 2). A simulated diffusion in the form of a random jump is superimposed on this motion to determine the location of the ion during the start of the next time-step. A more detailed discussion of the SDS algorithm is provided in the literature and in the SIMION 8.0 documentation. The SDS algorithm is capable of either using a defined mobility for each ion, or in the cases in which this data is not available, known information (particle diameters, masses, etc.) is used to estimate a value for ion mobility. Spatial variations in gas flow, pressure, and temperature may also be incorporated into the SDS algorithm to more accurately model conditions in which these parameters are known. Effects due to space charge can also be included in the modeling; however, ions must be flown as a group when incorporating space charge effects into an SDS simulation. For all simulations performed in this work, bulk gas flow was assumed to be zero and space charge was not considered in order to decrease computational time.

Example 3

Simulation of 2D Ion Distribution at Deposition Surface

The potential arrays (PA) used in the simulation of both the 2D ion distribution at the deposition surface (described below) and the separation of tetraalkylammonium (TAA) cations (described below) were generated from .stl format using the "Convert STL->PA" option in the SIMION 8.0 SL Tools. A 0.2 mm/grid unit resolution was selected to mimic the 0.2 mm layer height resolution at which the electrodes were printed and the solid strategy was set as "solid points under surface normal".

For the simulation of the mesh used for ion injection in the TAA cation separation, the mesh was modeled as a plane with a thickness equal to the grid cell size (0.2 mm). Because SIMION treats a plane of 1 grid unit as a 100% transmission ideal grid, this means that the simulated mesh passes ions at all points. This simplification was made to decrease computational time in the simulation as a smaller unit cell size (<0.2 mm/grid unit) is required to model the woven mesh in its true form which would result in a much larger PA space.

In the case of the simulated 2D ion distribution at the deposition surface, ions were initiated with a 3D Gaussian distribution ($\sigma_x$, $\sigma_y$, and $\sigma_z$=5 mm) in the center of the source electrode with a single time of birth (TOB). The contour plots of simulated ion distribution (FIGS. 2c and 2d) were generated using a histogram bin width of 0.05 mm×0.05 mm.

The simulation of ion separation was performed by initiating all ions with a uniform cylindrical distribution within the area between the two mesh electrodes. At the start of the simulation time step, the injection voltage was set to the high value used for injection (2530 V) for 50 ms, after which it was set to the low value (2480 V) for the remainder of the simulation time period. This approach is not meant to accurately model the ion distribution between the mesh electrodes during the injection, but is used to simplify the simulation so that arrival times of ions at the detector (a mass spectrometer in this case) can be approximated to determine if simulation values agree with experimental data.

Example 4

Electrode and Spacer Dimensions

Figure 5A:
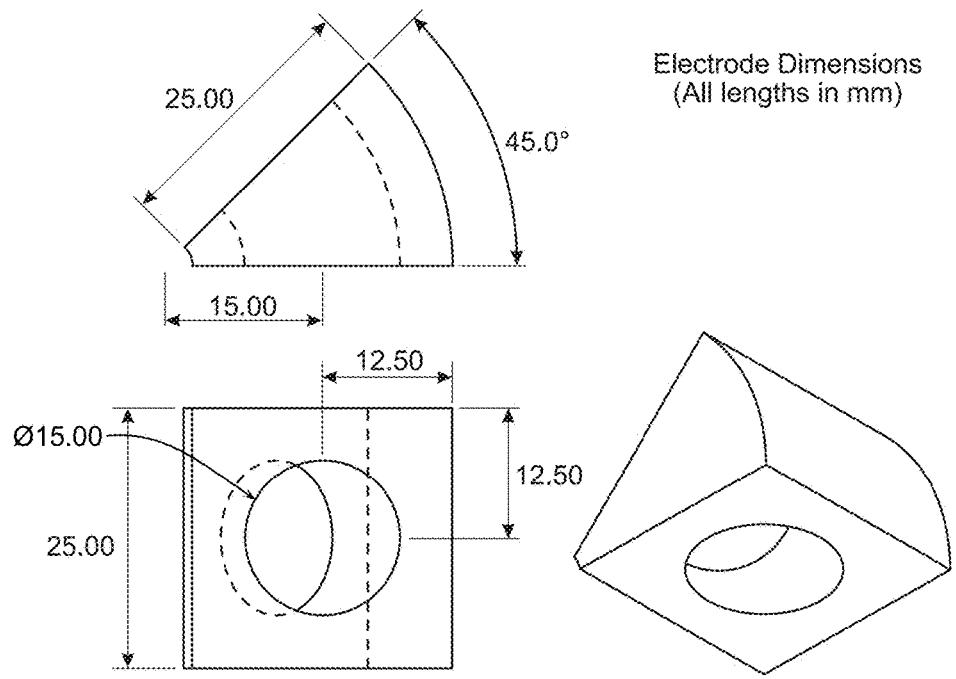
FIGS. 5A-C show dimensional drawings of turning electrodes (FIG. 5A), source electrode (FIG. 5B), and spacers (FIG. 5B).
Figure 5B:
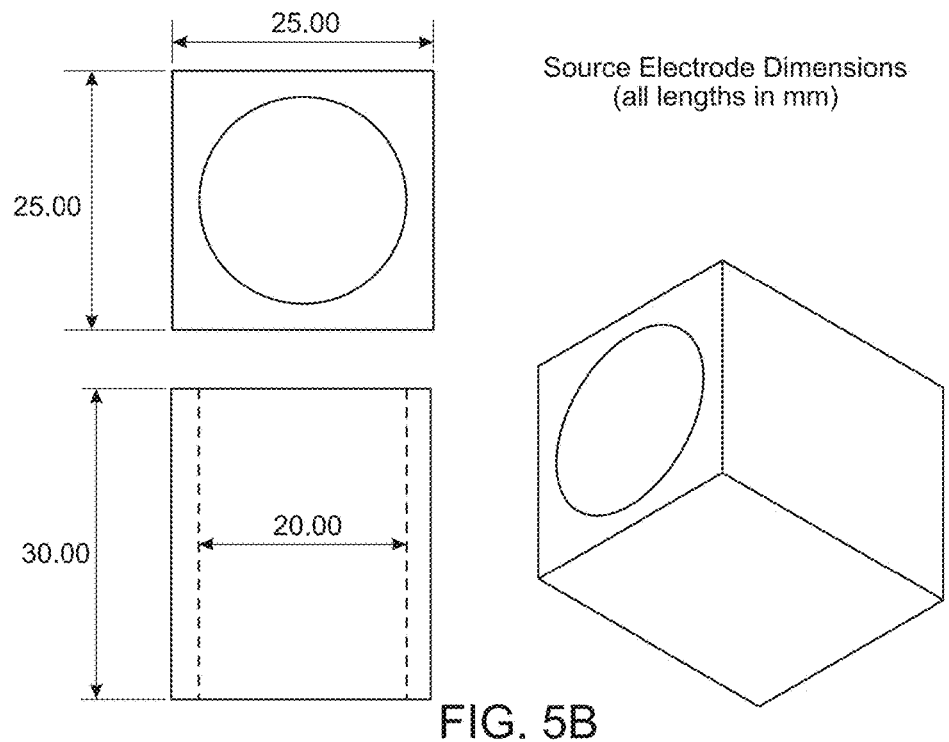
Figure 5C:
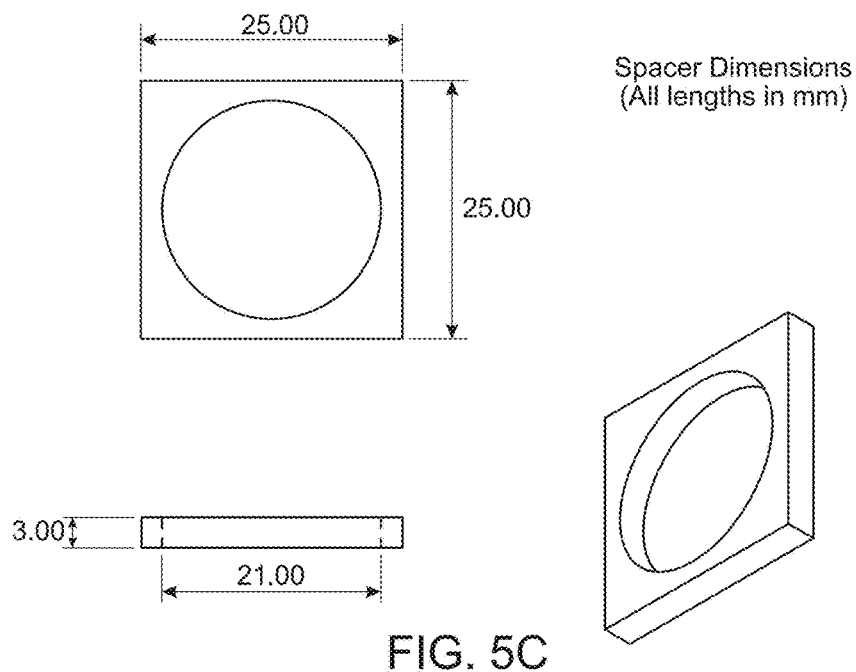

FIGS. 5A-C show dimensional drawings of turning electrodes (FIG. 5A), source electrode (FIG. 5B), and spacers (FIG. 5C).

Example 5

Ion Injector

Injection of ions into the turning electrodes was accomplished by modifying the electrode system to include a region separated by two wire meshes (FIG. 4B). The mesh closest to the source electrode was held at a low value of 2480 V which prevented the transmission of ions into the curved electrodes. Ions were injected into the curved electrode region by pulsing this voltage to a value of 2530 V for 50 ms.

Example 6

Profiling of Beam Using IONCCD (Atmospheric Pressure Ion Detector, Commercially Available from OI Analytical)

Figure 6:
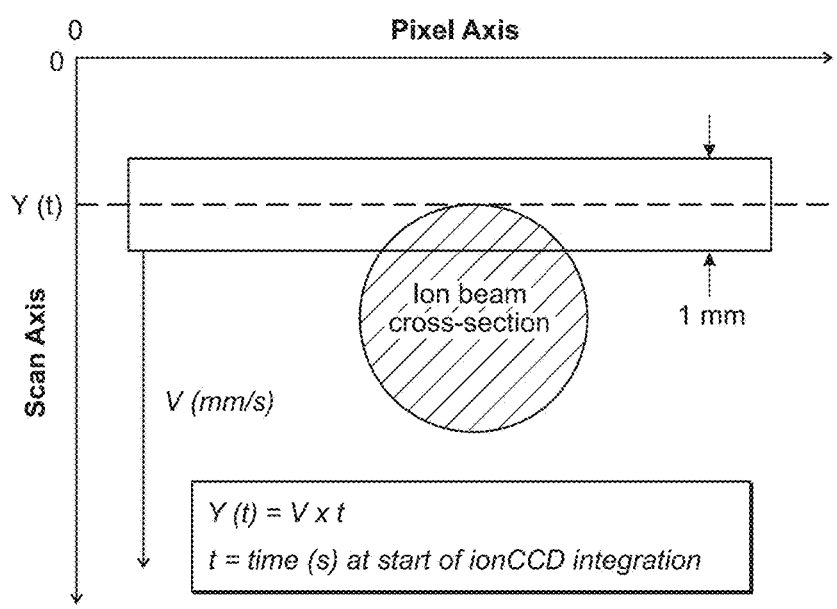
FIG. 6 is a diagram illustrating how IONCCD (atmospheric pressure ion detector, commercially available from OI Analytical) data was captured and the data assembled into a 2D plot of ion intensity from individual integration time steps. The detector slit is indicated by the blue transparent box.
Figure 7B:
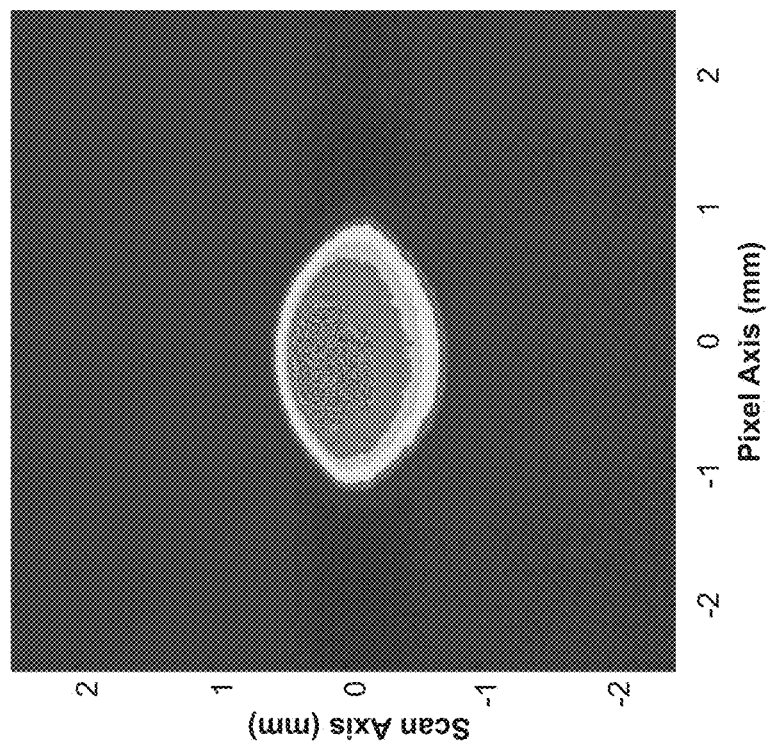
FIGS. 7A-D show experimental (FIGS. 7A-B) and simulated (FIGS. 7C-D) tetraalkylmmonium ion intensity at deposition surface for different electrode potentials. In panels A and C potentials on electrodes $E_1$, $E_2$, and $E_3$ were 2.90 kV, 2.60 kV, and 1.80 kV, respectively; in panels B and D potentials on electrodes $E_1$, $E_2$, and $E_3$ were 2.95 kV, 2.12 kV, and 1.77 kV, respectively. In each case $E_{source}$ was set to 3.00 kV and spray potential was set at 4.65 kV.
Figure 7A:
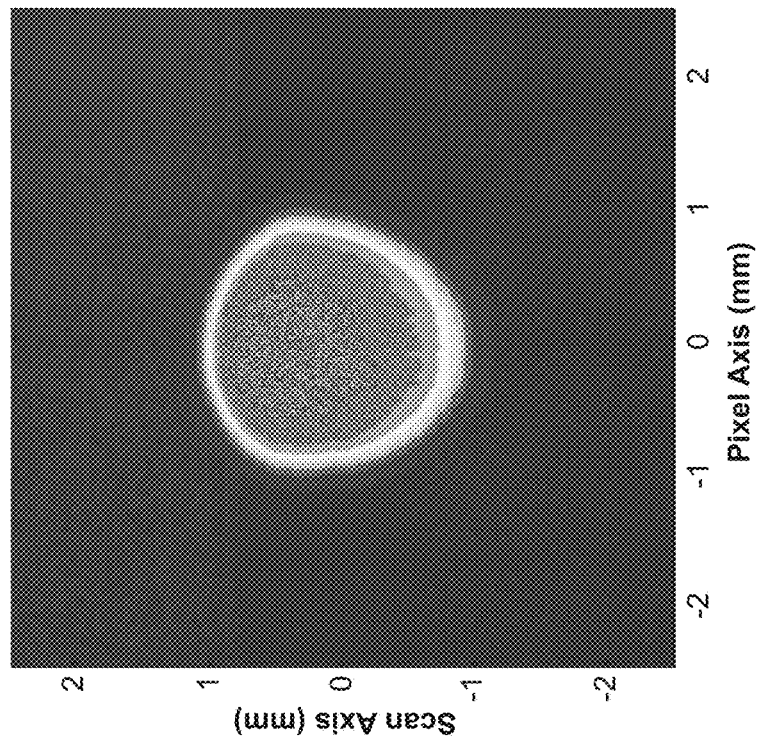
Figure 7D:
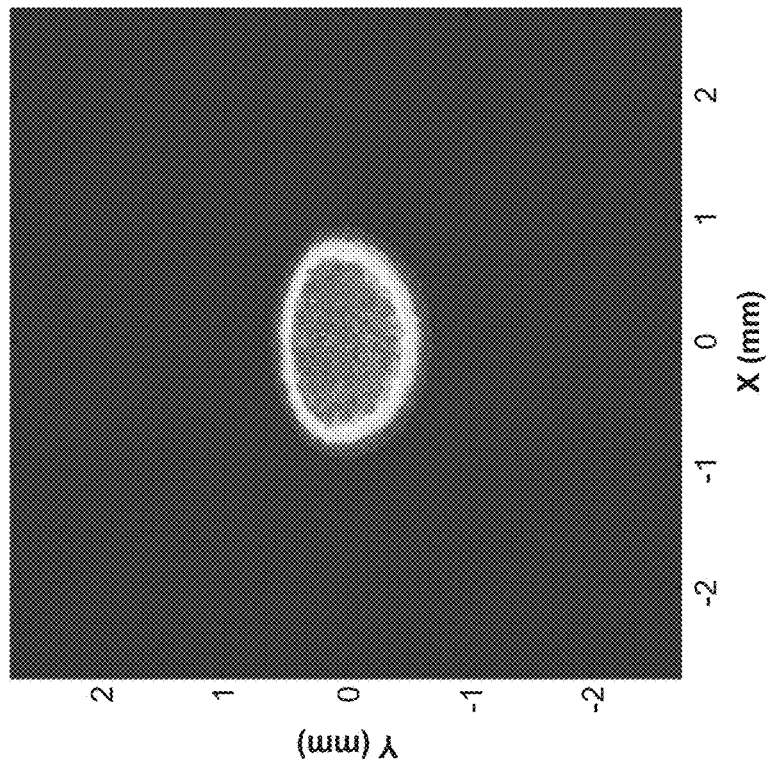
Figure 7C:
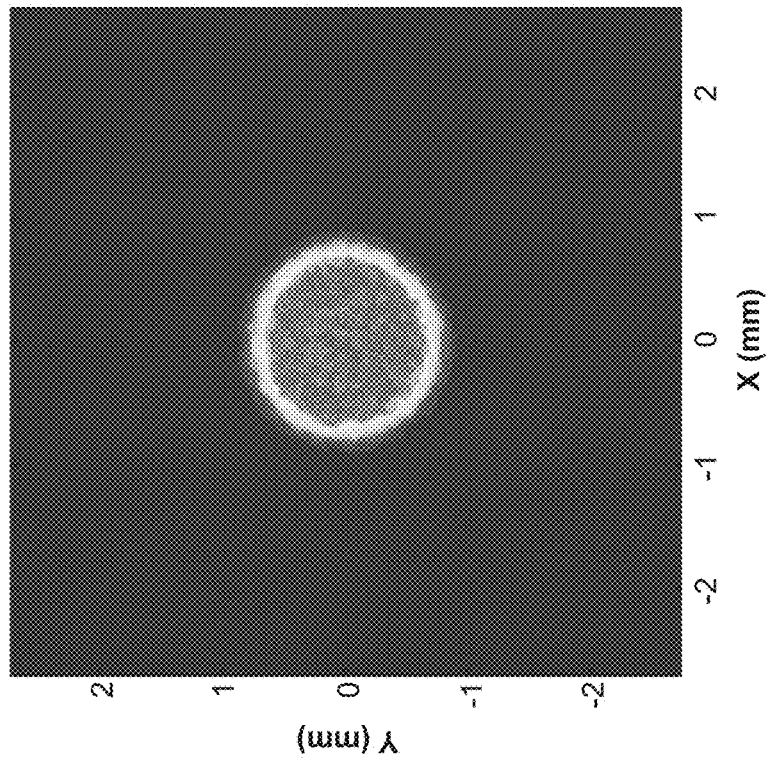

The ion beam exiting the electrode assembly was profiled by mounting the IONCCD (atmospheric pressure ion detector, commercially available from OI Analytical) detector on a moving stage and scanning the detector slit across the exit of the last electrode at a fixed rate of 0.100 mm/s. A diagram of this process is shown in FIG. 6. A potential of 10 V was applied to the detector housing during the signal acquisition. This potential served to increase the electric field strength between the floated detector array and the aluminum enclosure (0.711 mm gap between housing and detector array), thus drawing ions to the detector surface which results in a stronger signal.

The 2D intensity plots were reconstructed from the data by a Matlab script which uses the integration time (100 ms in all experiments) along with the velocity of the moving stage to calculate position along the scan axis (Y(t)) for each detection cycle of the detector.

The elongation seen in the reconstructed intensity plots (FIGS. 7A-D) when compared to the simulated 2D ion distribution at the electrode exit is likely a result of both the gap between the stainless steel housing and the detector surface as well as the width of the pixel array (1 mm). The elongation in the pixel axis is likely the result of ions diffusing outward after entering the gap between the housing and the detector surface. The 10 V potential serves to negate this effect slightly, but application of larger potentials poses the risk of damaging the detector electronics. The width of the pixels most certainly contributes to an elongation in the reconstructed signal intensity along the scan axis. For example, at a scan rate of 0.100 mm/s the detector slit moves approximately 0.100 mm during an integration time step which is only 10% of the pixel width. This means that the position assigned to each integration time step along the scan axis also includes the entirety of ions exiting the electrode ±500 µm from the assigned position (Y(t)).

Example 7

System Configuration

A curved electrode system was constructed from a conductive polymer using a fused deposition modelling (FDM) 3D printer. The assembly consists of a cylindrical source electrode region ($E_{source}$) with an inner diameter (ID) of 20 mm and a length of 30 mm, proceeded by 3 curved electrodes ($E_n$) with an ID of 15 mm and a swept angle of 45 degrees around a 15 mm radius of curvature. All electrodes are separated by 3 mm with spacers printed in either acrylonitrile butadiene styrene (ABS) or polylactic acid (PLA). Dimensional drawings are provided in FIG. 5. The electrode assembly (FIG. 1A) serves to focus ions from a spray source to a well-defined region with the application of an appropriate potential gradient along the ion path. The device is shown in FIG. 1A interfaced with the inlet of a mass spectrometer along with a cutaway rendering with an overlay of simulated ion trajectories (FIG. 1B). The curvature of the ion path greatly reduces the probability of neutral transmission by avoiding line-of-sight from the sprayer to the detection/deposition surface. Although this geometry is difficult to machine using traditional subtractive manufacturing techniques, it is trivial to produce by additive manufacturing methods such as FDM. FDM is a process by which a plastic filament is extruded through a heated nozzle to form an object one layer at a time (Gibson et al., Springer US, 2010, pp. 160-186). Common materials used in FDM include ABS, PLA, polyamide (nylon), polyethylene terephthalate (PET), polycarbonate (PC), etc. FDM was chosen for the construction of the electrode assembly because of its low cost, the availability of a range of materials, and the rapid nature in which the parts could be produced; the entire assembly could be constructed in under 3 hours.

Simulations of ion trajectories within the device were performed with SIMION 8.0 (Scientific Instrument Services) and the included statistical diffusion simulation (SDS) algorithm (further described in Example 1 above). At atmospheric pressure, it is not computationally efficient to utilize traditional hard-sphere collision models as the mean free path in air is ~67 nm. Instead, the SDS algorithm calculates ion motion based on ion mobility and a simulated diffusion in the form of "jumps" in a random direction at each time step, the magnitude of which is determined based on collision statistics. A more detailed discussion of ion trajectory simulation at atmospheric pressure and details of simulation parameters used are included in Example 1. The workflow from design to simulation involved the use of the SL toolkit included with SIMION. The SL toolkit allows the user to import geometry in the form of stereolithography (.stl) files to create potential array points which are the basis of the simulation environment in SIMION. Because .stl is the native file format accepted by most software packages to prepare files for 3D printing, the same files may be used for both electrode production and trajectory simulation.

Example 8

System Validation

The ability to generate, transmit, focus, and detect ions in air with the curved polymeric electrode system was demonstrated by spraying a mixture of tetralkylammonium (TAA) bromide salts (10 µM in acetonitrile) from a nanoESI emitter into the source region ($E_{source}$) of the curved electrode. Plots of ion intensity at the exit region of the curved electrode system were reconstructed from data obtained by scanning an IONCCD (atmospheric pressure ion detector, commercially available from OI Analytical) detector across the exit orifice of the final electrode at a fixed rate (FIG. 6). Reconstructed intensity plots are shown in FIGS. 7A-D along with the simulated ion intensities under the same conditions.

Differences in the reconstructed intensity vs. the simulated intensity can be largely attributed to scanning artefacts due to the width of the IONCCD (atmospheric pressure ion detector, commercially available from OI Analytical) pixels and the stainless steel housing of the IONCCD (atmospheric pressure ion detector, commercially available from OI Analytical). Moreover, the true distribution of ions near the emitter tip is unknown and for simplification purposes ions were initiated with 3D Gaussian distribution ($\sigma_{xyz}$=5 mm) in the source region and no simulations took space charge into account. The data show that simulated and experimental ion intensities are in good agreement, which highlights the utility of the SIMION-SDS algorithm in predicting the performance of the 3D printed polymeric electrodes.

Example 9

Separation of Ions in Air

The separation of gas-phase ions is most commonly done based on their mass-to-charge ratio (m/z), in the case of MS, or on the basis of their interaction with a background gas in combination with electric fields as is done in IMS experiments. A vacuum is necessary in order to accomplish separation based on m/z, while a laminar flowing gas is used in the instance of an ion mobility separation.

Systems of the invention are able to perform separation of ions in air without the use of a vacuum or a flowing gas.

Instead, pulsed voltages were employed with the electrode system as a means to inject ions into the curved ion path and effect a separation of tetraalkylammonium (TAA) cations. A solution of 10 μM each of tetrapropyl-, tetrabutyl-, tetrahexyl-, and tetradodecylammonium bromide in ACN was sprayed with a nanoESI emitter into $E_{source}$. The electrode assembly was modified to include an injection region immediately after $E_{source}$ consisting of 2 stainless steel woven meshes separated by 3 mm (FIG. 4 panel B). A floated high voltage pulse (2530 V high, 2480 V low) was applied to the mesh directly after the source region with the second mesh held flush to the opening of the first curved electrode to facilitate electrical contact with $E_1$ (FIG. 4B). A pulse width of 50 ms with a repetition rate of 1 Hz was used for ion injection. Potentials applied to the nanoESI electrode, $E_{source}$, $E_1$, $E_2$, and $E_3$ were 4.50 kV, 3.20 kV, 2.50 kV, 2.33 kV, and 1.45 kV, respectively.

Figure 8:
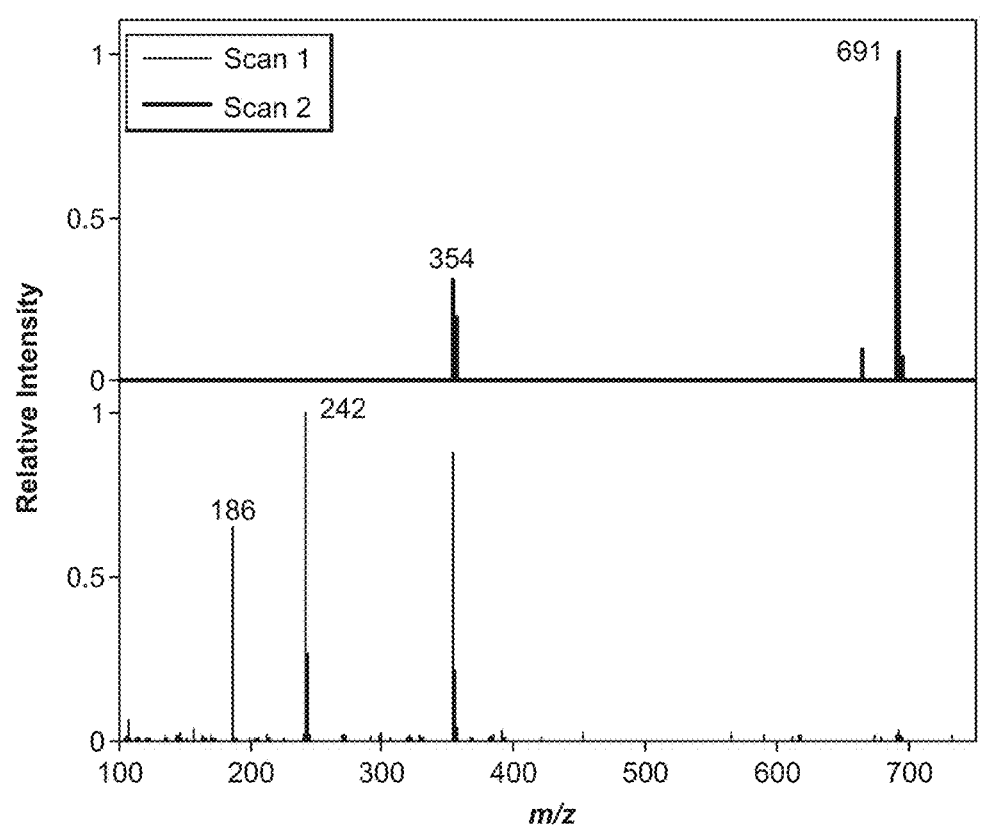
FIG. 8 is mass spectra of tetraalkyl ammonium cations from consecutive MS scans.
Figure 9:
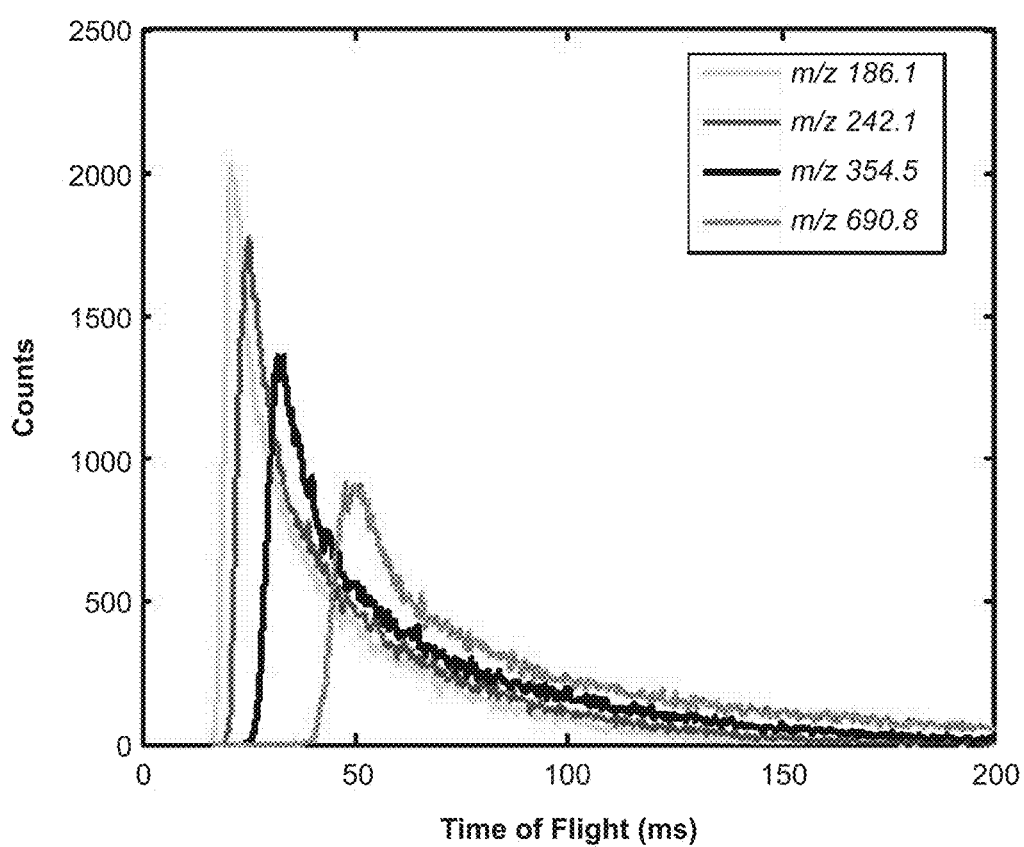
FIG. 9 a graph showing simulated time of flight distribution for tetraalkylammonium cation mixture transmitted through printed electrode assembly.

A simulation of the separation was performed under identical conditions with all ions originating in the space between the woven meshes. Consecutive scans of the ion trap (FIG. 8) at a 10 Hz scan frequency show separation of the TAA cations which agree well with the simulated data (FIG. 9). This data shows the ability to separate gas-phase ions in air and highlights a use of the 3D printed electrodes.

Figures 10A, 10B, 10C:
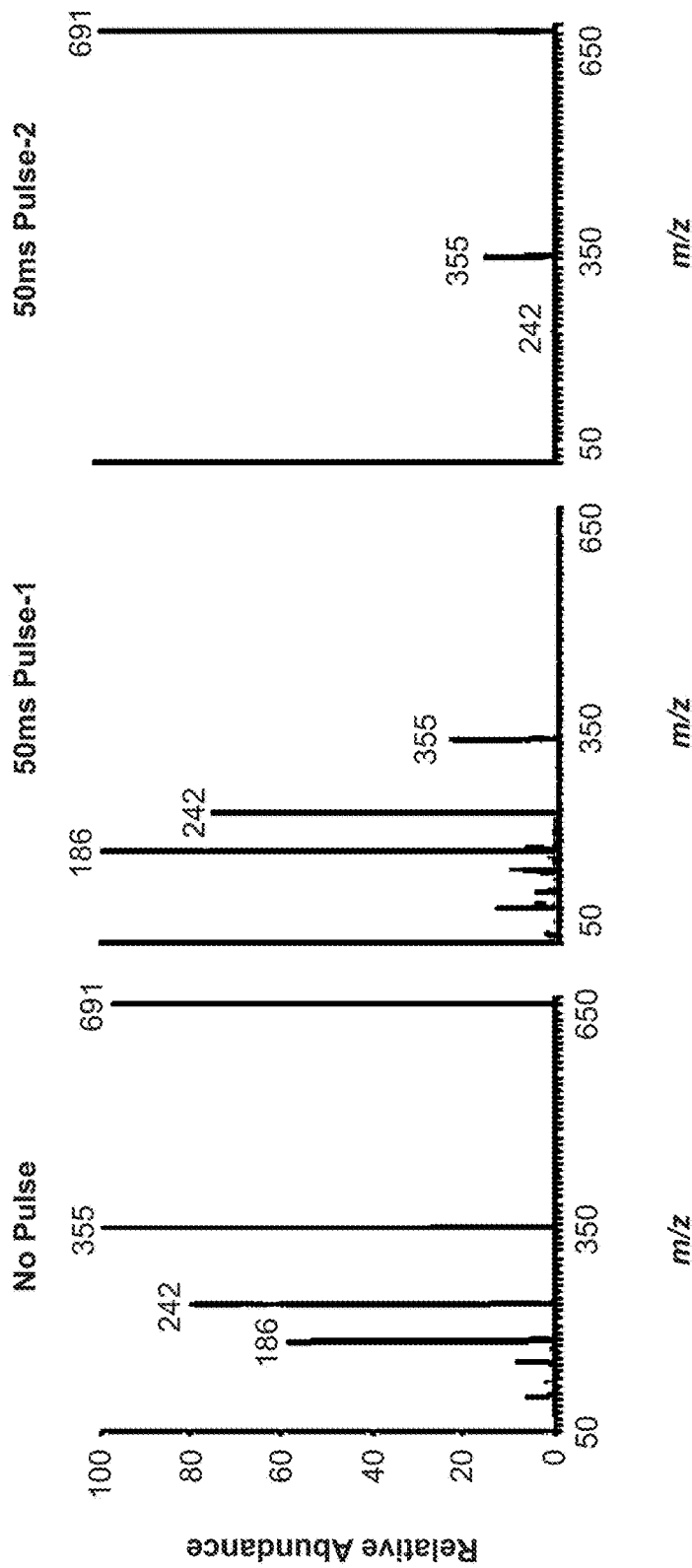
FIG. 10A is additional data showing separation of tetraalkyl ammonium cations ($C_3$, $C_4$, $C_6$, $C_{12}$) by applying a square wave, floated high voltage pulse (2950 V high, 2935 V low) to the source electrode. Spectra in FIGS. 10B-C are subsequent scans from the trap at a 7.7 Hz acquisition rate.

FIG. 10A is additional data showing separation of tetraalkyl ammonium cations ($C_3$, $C_4$, $C_6$, $C_{12}$) by applying a square wave, floated high voltage pulse (2950 V high, 2935 V low) to the source electrode. Spectra in FIGS. 10B-C are subsequent scans from the trap at a 7.7 Hz acquisition rate.

Example 10

Ion/Molecule Reactions

Ion/molecule reactions (IMR) have been shown to have useful analytical characteristics, especially in the case of structural elucidation. IMRs in the gas phase offer several benefits compared to their solution counterparts. Very little neutral reagent is required for an IMR and often the headspace vapour is sufficient to generate measurable product. Reaction rates and efficiencies are also inherently high for most IMRs, meaning that analytes in trace quantities will still form a detectable product. This is especially true for IMRs performed at atmospheric pressure in IMS instruments, as the number of collisions per second is dramatically increased in comparison to the same reaction performed in an ion trap under vacuum. However, the lack of straightforward identification of products in IMS generally requires the use of tandem IMS-MS instrumentation. Often, significant modification to MS instruments must be made in order to perform ion/molecule reactions, which can be costly and time-consuming. The coupling of IMS to MS instruments suffers from similar drawbacks.

The data herein demonstrate an ion-molecule reaction performed with the plastic electrodes in air, protonated tert-butylamine and cyclohexylamine ions were generated by nanoESI from 10 ppm solutions in methanol and reacted with dimethyl methylphosphonate (DMMP) in the last region ($E_3$) of the electrode system shown in FIG. 1A. DMMP vapor was introduced by replacing the final electrode with an electrode containing a hole on the far side of the swept radius of curvature (FIG. 4A) and inserting a cotton swap saturated with a solution of 1000 μg/mL DMMP in methanol (FIG. 1A). The electrodes were positioned with a 3 axis moving stage such that the exiting ions were sampled with the API of an LTQ linear ion trap (Thermo).

Figure 11A:
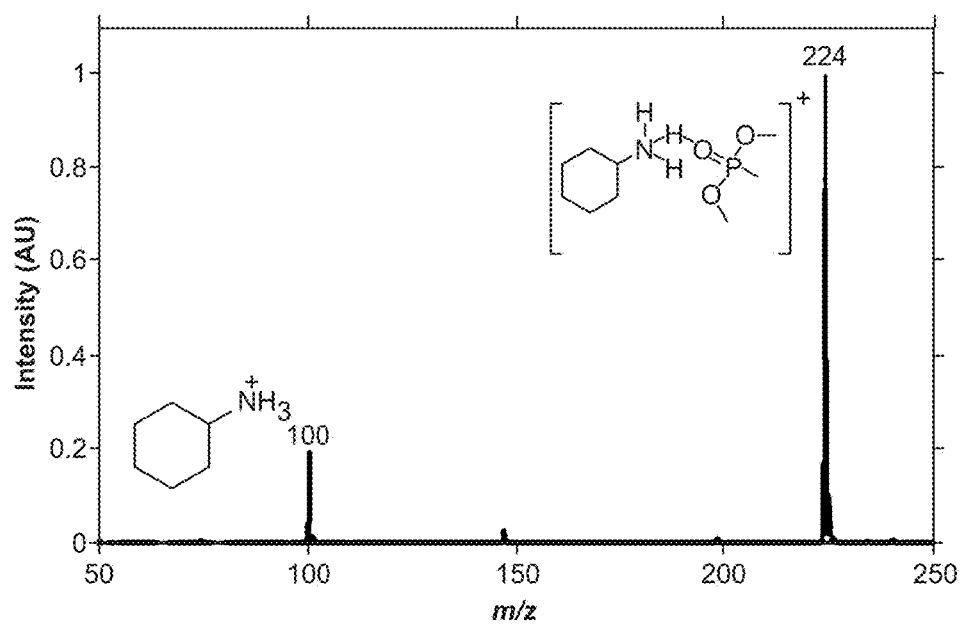
FIGS. 11A-B are mass spectra showing reaction of protonated cyclohexylamine with DMMP vapor (FIG. 11A) and tert-butylamine with DMMP vapor (FIG. 11B).
Figure 11B:
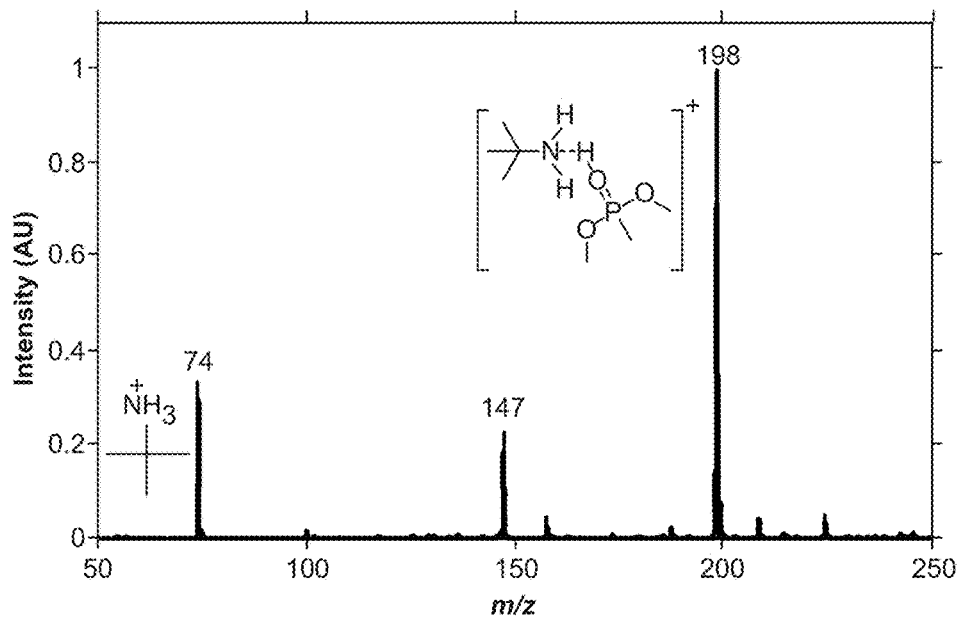

When the ion beam exiting the electrode structure was precisely aligned with the inlet of the MS it was found that the signal recorded by the mass spectrometer was largely independent of the position of the nanoESI spray tip within $E_{source}$ as the mass spectra and recorded intensity remained stable while adjusting the spray tip location. Mass spectra of the products of these two reactions sampled from the last electrode of the polymeric electrode assembly are shown in FIG. 11. Similar IMRs using analogs of DMMP have previously been demonstrated for the identification of amino functionalities in a Fourier transform ion cyclotron resonance (FT-ICR) mass spectrometer. These reactions highlight the potential usefulness of ion manipulation outside the mass spectrometer in exploring ion/molecule reactions for functional group identification. The ability to perform and interrogate these reactions outside the MS may allow for a condition in which an ion separation is performed at atmospheric pressure after a reaction has taken place to identify the presence of a target compound in the analyte mixture.

Figures 12A, 12B:
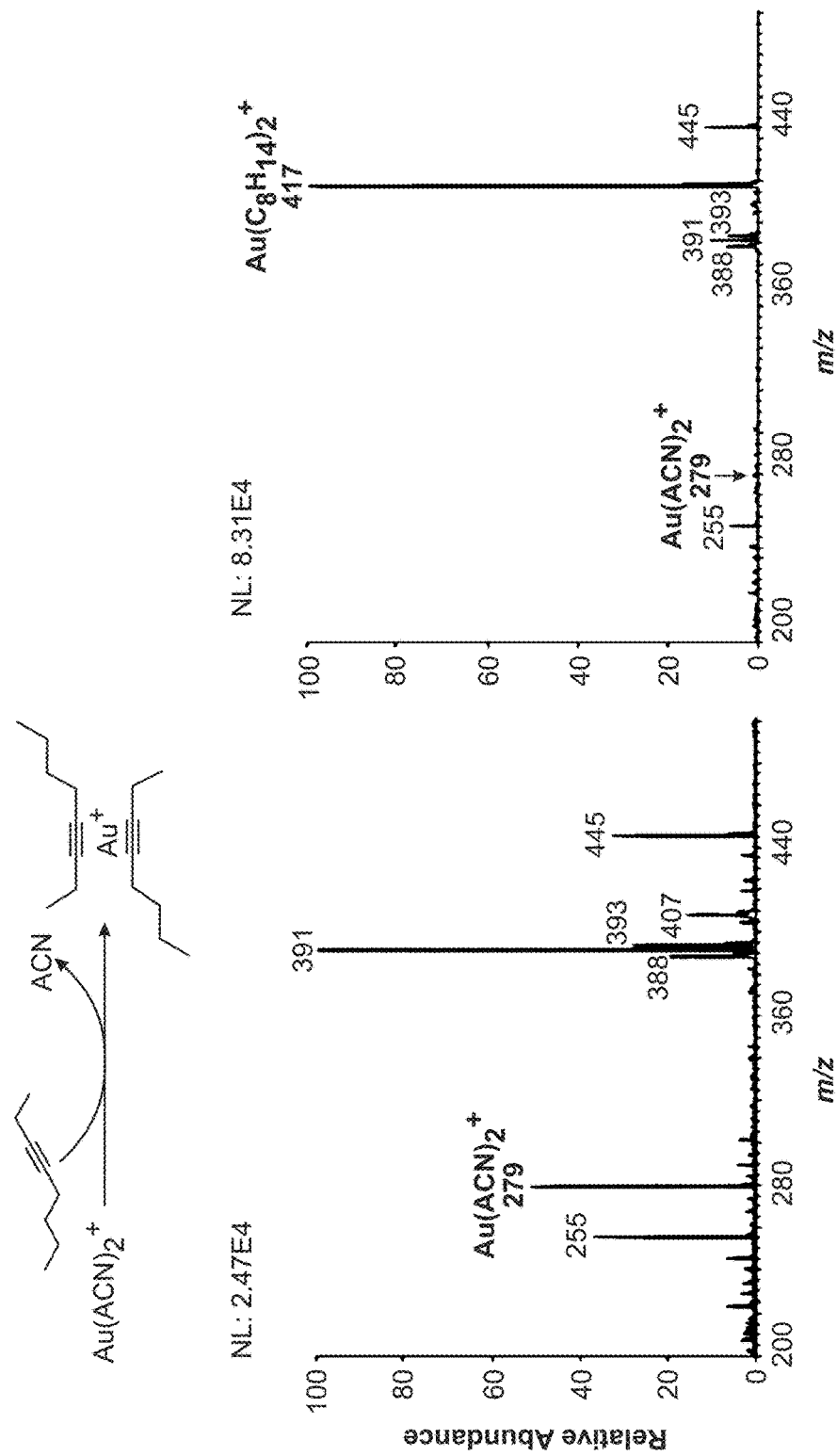
FIGS. 12A-B are spectra of the ion-molecule reaction in air using electrolytic nanoESI (Au electrode) to generate Au(ACN)$^{2+}$ from acetonitrile (ACN) spray solvent Neutral: 3-octyne on cotton swab (Ion detection: Thermo LTQ).

Another ion/molecule reaction was performed using vapor of 3-octyne as the neutral molecule supplied by evaporation from a swab placed near the 3rd turning electrode. The reacting ions were Au[CH$_3$CN]$^{2+}$ generated by electrolytic spray ionization from a gold electrode in acetonitrile. The product ions were the bis-ligated 3-octyne and it quantitatively replaced the bis-acetonitrile FIGS. 12A-B). FIGS. 12A-B are spectra of the ion-molecule reaction in air using electrolytic nanoESI (Au electrode) to generate Au(ACN)$^{2+}$ from acetonitrile (ACN) spray solvent Neutral: 3-octyne on cotton swab (Ion detection: Thermo LTQ). Referring still to FIGS. 12A-B, the ion-molecule reaction is shown above the spectra. Note in FIGS. 12A-B the presence of unassigned ions in the reagent ion spectrum. These do not react so occur unchanged in the product spectrum.

Example 11

Figure 13:
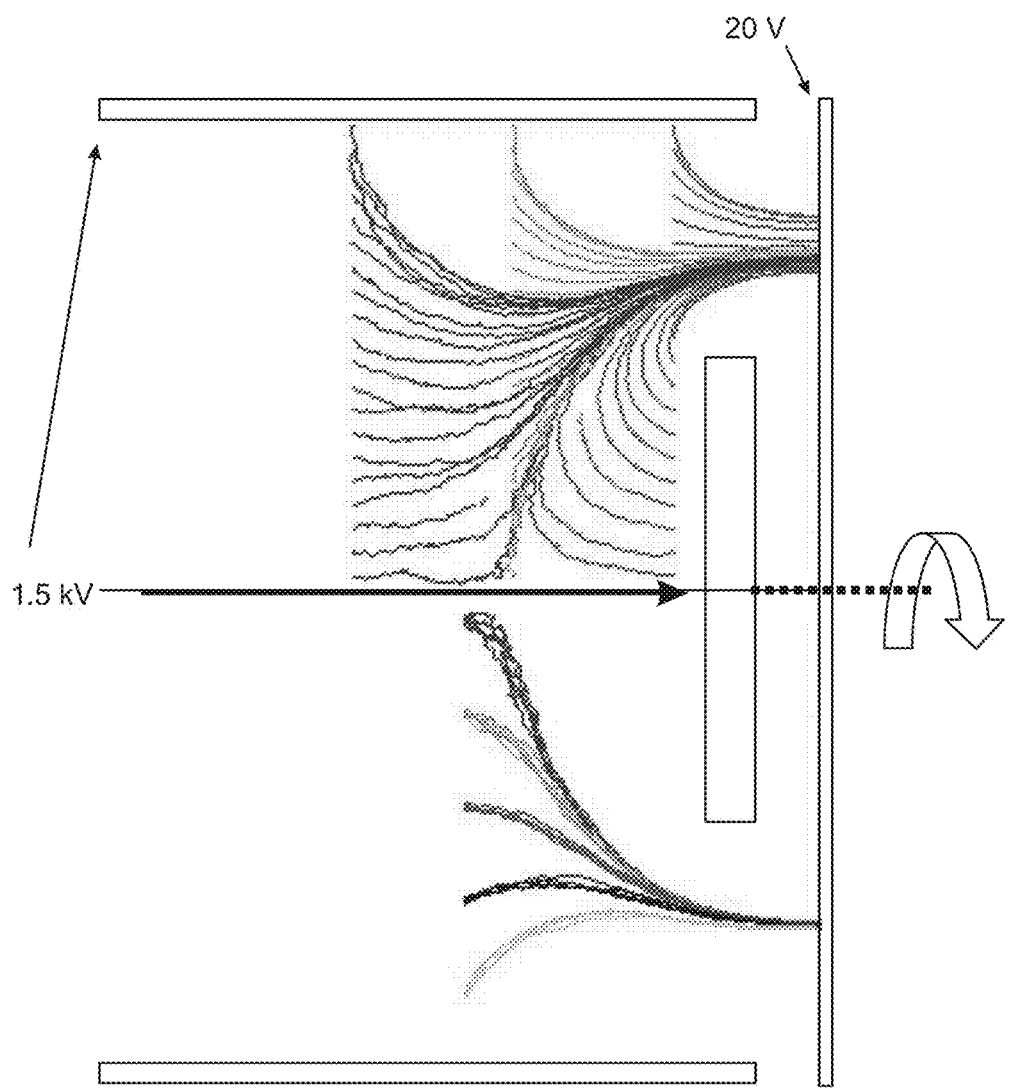
FIG. 13 illustrates simulated ion trajectories within a cylindrical electrode with a coaxial disc electrode, each held at a potential of 1.5 kV in close proximity to a surface with a potential of 20 V. Dotted line and arrow are drawn to show axis of cylindrical symmetry.

Focusing of Ions in Air Using a Cylindrical Electrode with a Coaxial Disc Electrode FIG. 13 illustrates simulated ion trajectories of protonated acetonitrile ions in a cylinder of 30 mm inner diameter that incorporates a coaxial disc electrode of 15 mm diameter and 1.6 mm thick positioned flush to the end of the cylinder. Both the disc and cylinder are held at the same potential. When these coaxial electrodes are positioned in close proximity to a surface held at a significantly lower potential (100V down to several kV lower), electric fields are created that cause ions to be focused to an annulus with a diameter that is largely dictated by the diameters of the central disc and outer cylinder. From here on, this configuration of electrodes and application of appropriate potentials will be referred to as a radial ion lens. Simulated and experimental data also show that the potential offset (between electrode components and deposition/detection surface) also affects both the line width of the annulus, as well as the diameter.

This radial ion lens and the type of focused ring of ions it produces are of particular interest in cases where spray ionization may be used to modify a surface, deposit material onto a surface, and introduce ions into a mass spectrometer or an ion mobility spectrometer as it eliminates line-of-sight from the spray emitter to the surface, detector, or other such target as they are physically blocked by the inner disc. This prevents the contamination of the surface, detector, or target with neutral species or large droplets. Additionally, this may serve as a jet-disruptor (perturbs high velocity gas streams to limit interference with static gas within the subsequent ion optics) in cases where a nebulizing, or carrier gas is used in the generation of ions or their subsequent transfer to a surface, target, or detector.

Figure 14A:
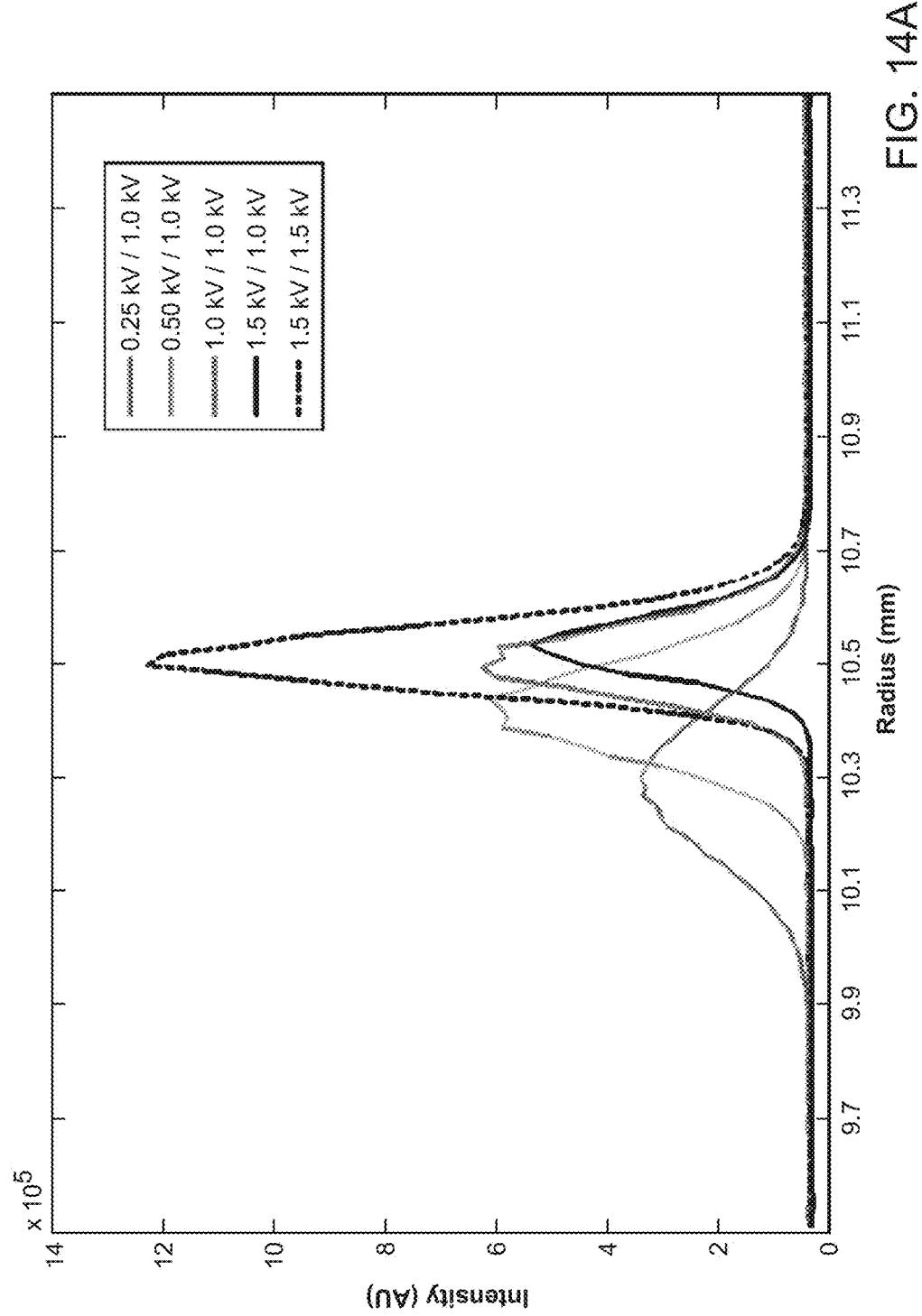
FIGS. 14A-C show radial intensity of ions focused into an annulus under varied conditions.
Figure 14B:
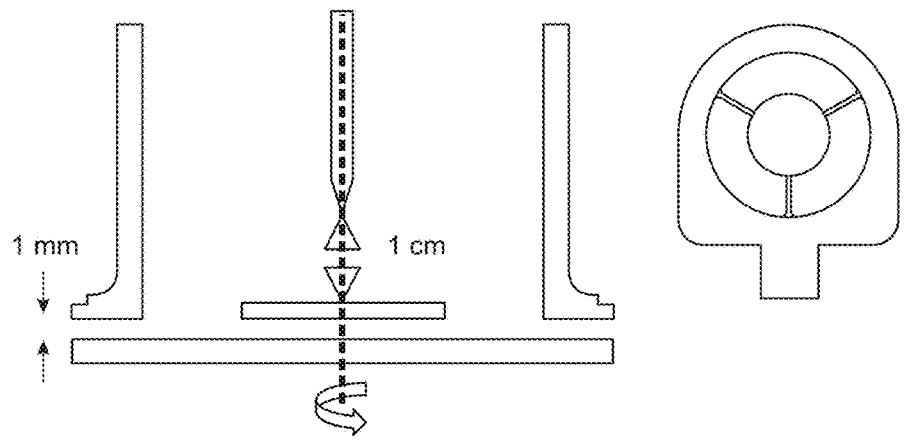
Figure 14C:
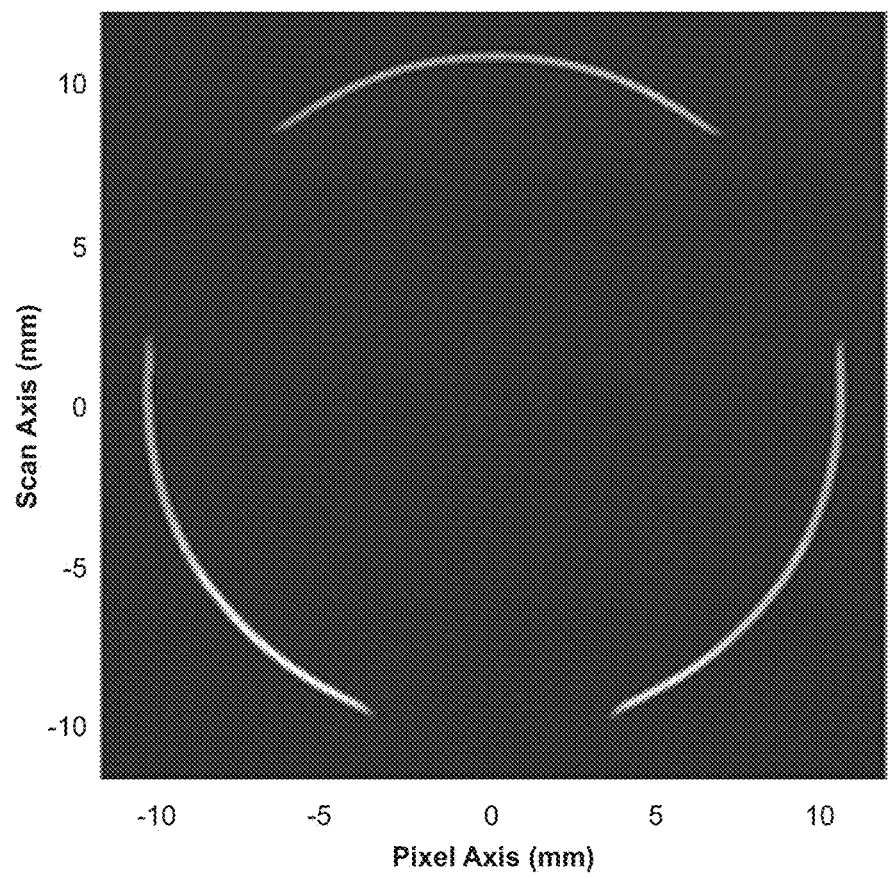

FIG. 14A shows the radial intensity of ions at a grounded deposition surface positioned approximately 1 mm from the opening of the radial ion lens as was determined experimentally from reconstructed two dimensional ion images obtained by scanning a pixelated charge detector across the opening of lens as was described previously. The traces obtained in FIG. 14A were obtained by fitting a circle to a two dimensional plot of ion intensity (such as that shown in FIG. 14C, centering the data using the center of the fit circle, and converting ion intensity into polar coordinates. A histogram plot of the radial ion intensity was then made under various experimental conditions. The first number in the legend displayed in FIG. 14A represents the potential difference between the radial ion lens and the detection surface with the second number representing the potential applied to the nanoelectrospray ion source in relation to the first number (i.e. 0.25 kV/1 kV is the case in which 250 V was applied to the radial ion lens and a potential of 1.25 kV was applied to the nanoelectrospray emitter). FIG. 14B shows a simplified version of the experimental setup as well as a top down view of the radial ion lens. Small filaments are used to connect the central disc to the walls of the cylinder.

Figure 15:
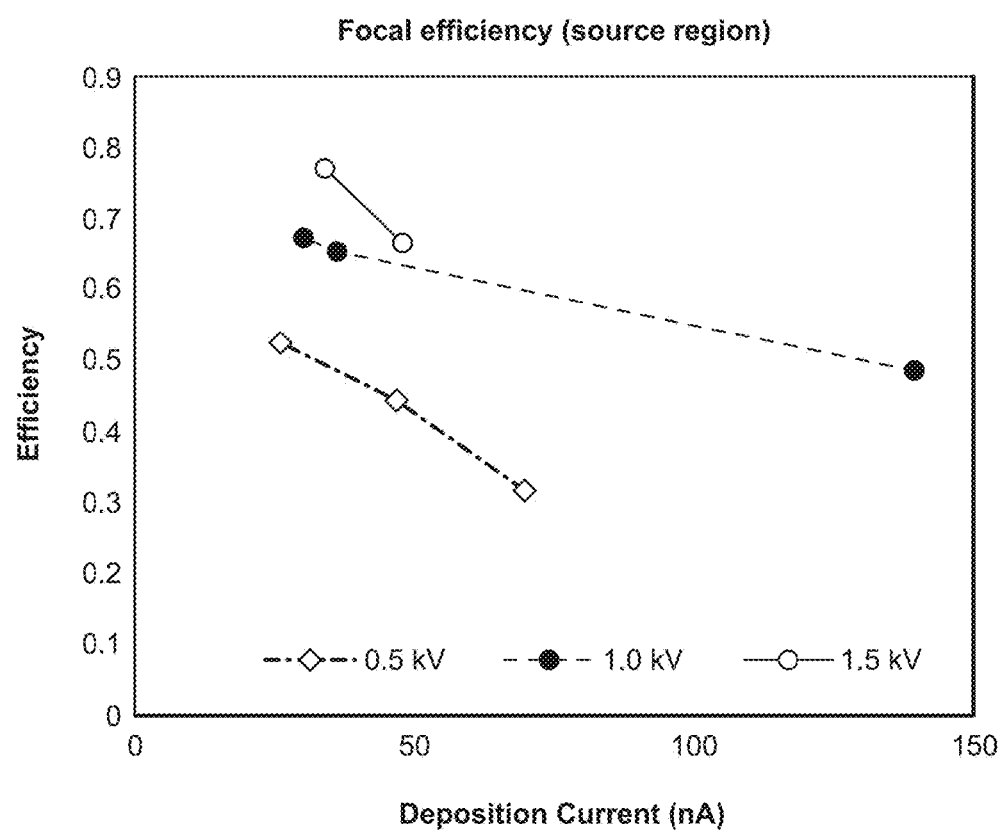
FIG. 15 is a graph showing efficiency of ion transfer from a nanoelectrospray ionization source to a grounded deposition surface by the radial ion lens with different applied potentials.

FIG. 15 is a graph showing efficiency of ion transfer from a nanoelectrospray ionization source to a grounded deposition surface by the radial ion lens with different applied potentials. The spray current for each data point shown in FIG. 15 was calculated by measuring a potential drop across a 4.7 MΩ resistor which by Ohm's law may be calculated using the equation shown below:

$$\text{Current }(A) = \frac{\text{Potential drop across resistor }(V)}{4.7 \times 10^6 \, \Omega}$$

The corresponding deposition current was measured using a picoammeter connected to a copper sheet used as the deposition surface. The efficiency was then taken by dividing the deposition current by the calculated spray current under a given condition. Different spray currents were achieved by adjusting the potential applied to a nanoelectrospray emitter filled with a 2 mM equimolar mixture of tetrabutyl-, tetrahexyl-, tertraoctyl-, and tetradodecylammonium halides in a solution of 4:1 methanol:acetonitrile with 0.1% formic acid. The spray emitter was positioned as shown in FIG. 14B.

Example 12 3D Printed Ion Mobility Spectrometer

Figure 16:
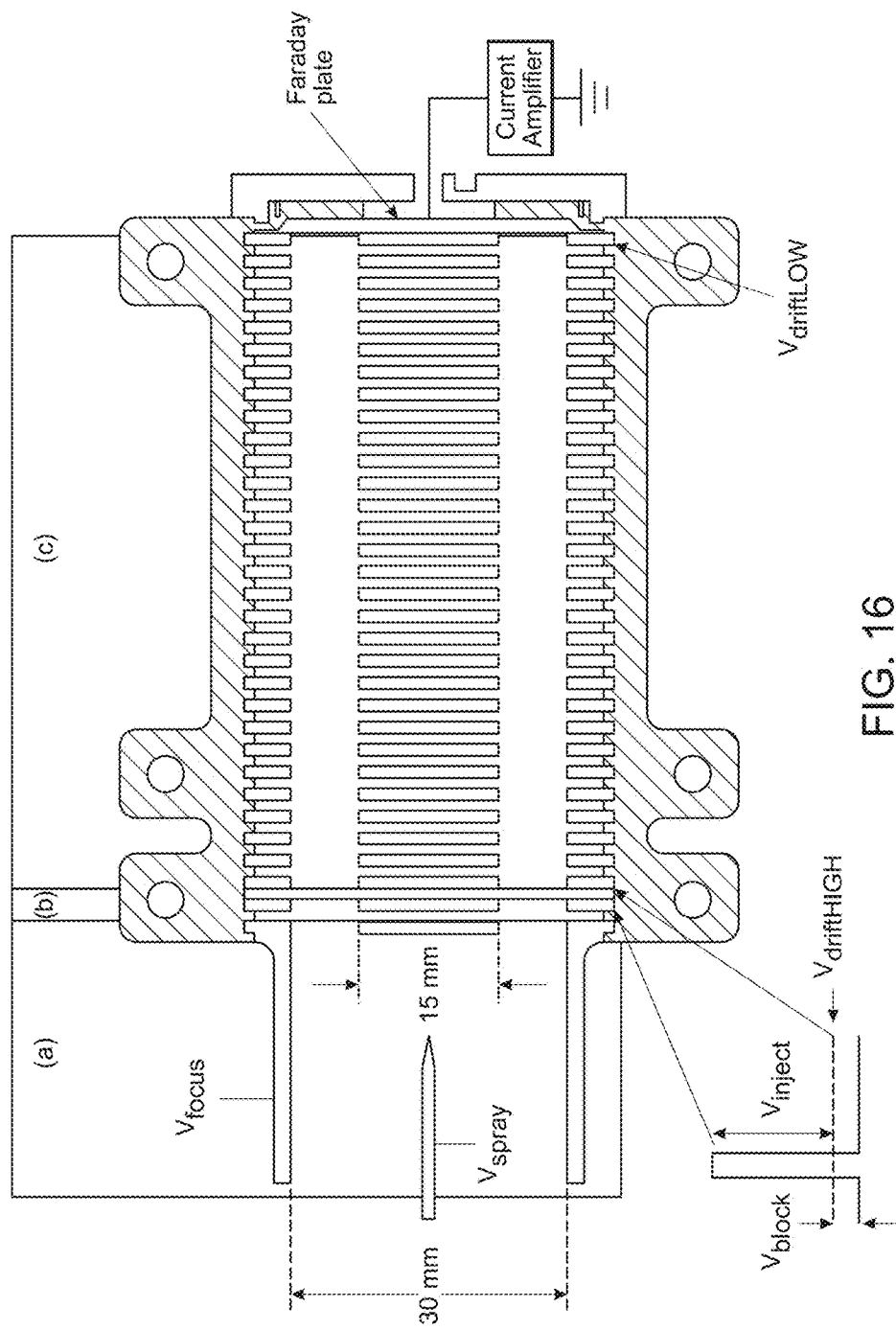
FIG. 16 is a cutaway view of a 3D printed ion mobility spectrometer.

A 3D printed ion mobility spectrometer (IMS) was constructed by fused deposition modeling. A glycol-modified polyethylene terephthalate (PETg) impregnated with carbon nanotubes was used for electrode components (shown as black in FIG. 16) and polylactic acid (PLA) was used to construct electrode housing components (shown as hatched in FIG. 16). The IMS consisted of 4 parts:

(a) A source/focal region that contained the nanoelectrospray ion source as well as the radial ion lens. This portion is shown as (a) in FIG. 16.

(b) An ion injection region consisting of an electrode with a stainless steel mesh held flush to the electrode on the side immediately preceding the drift cell and separated from the first drift electrode by a PLA spacer. Ion injection was achieved by applying a floated high voltage pulse the injection electrode. During the high portion of this pulse (typically 50-100 V in relation to the potential on the first drift ring) ions are extracted from the radial ion lens and injected into the drift cell. During the low portion of the pulse (typically −25 V in relation to the potential applied on the first drift electrode) ions are blocked from entering the drift cell. This portion is shown as (b) in FIG. 16.

(c) A drift cell consisting of 30 electrodes and separated by spacers incorporated in the housing assembly. A potential gradient is applied along the drift cell so as to create a uniform electric field which drives ions toward the detector region. The entrance and exit of the drift cell each incorporate a stainless steel mesh held flush with the surface. The mesh on the first drift electrode ensures the changing potential on the injection electrode does not interfere with the electric field within the drift region. The mesh on the final drift electrode serves to shield the detector surface from the approaching ion packets, greatly reducing effects due to an image charge on the detector surface. The exit electrode and mesh are generally held at a potential of 100-500 V relative to the grounded detection surface. This portion is shown as (c) in FIG. 16.

(d) The detection region consists of a Faraday plate constructed of a suitable conductor (in this case a copper sheet) which is connected to a current amplifier, read by an oscilloscope. The detector region is not limited to detection by this manner and may incorporate any manner of suitable charge detector capable of operating at atmospheric pressure or above.

Electrodes used for injection and drift cell construction were similar in design to the radial ion lens previously described; however, the height of the outer cylindrical portion was matched to that of the central disc.

Figure 17A:
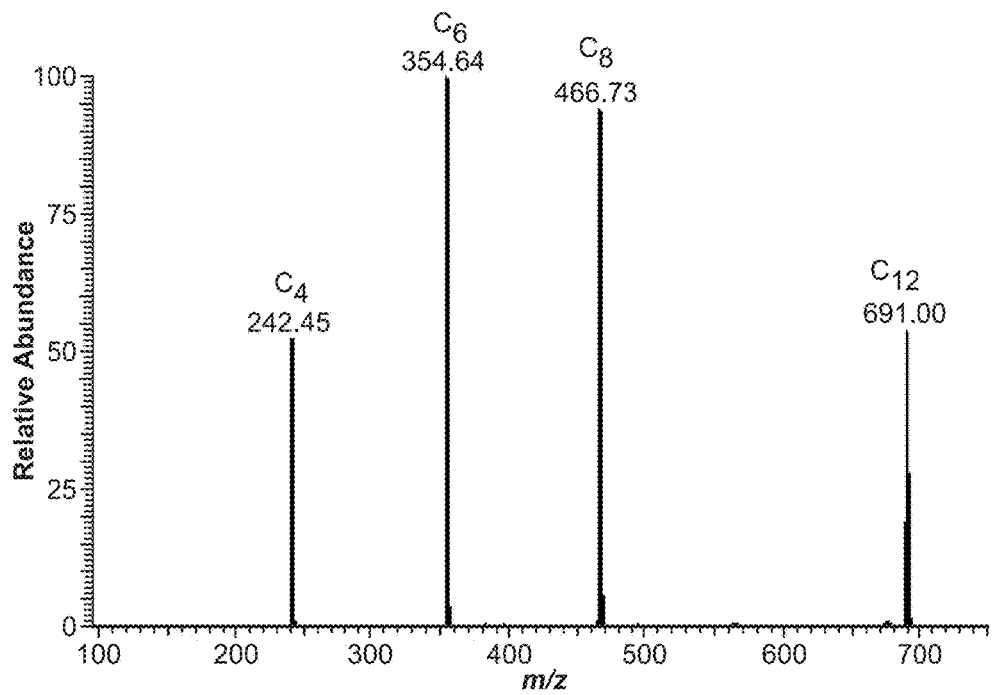
FIG. 17A shows a mass spectrum of a tetraalkylammonium cation mixture transmitted through 3D printed IMS without employing separation.
Figure 17B:
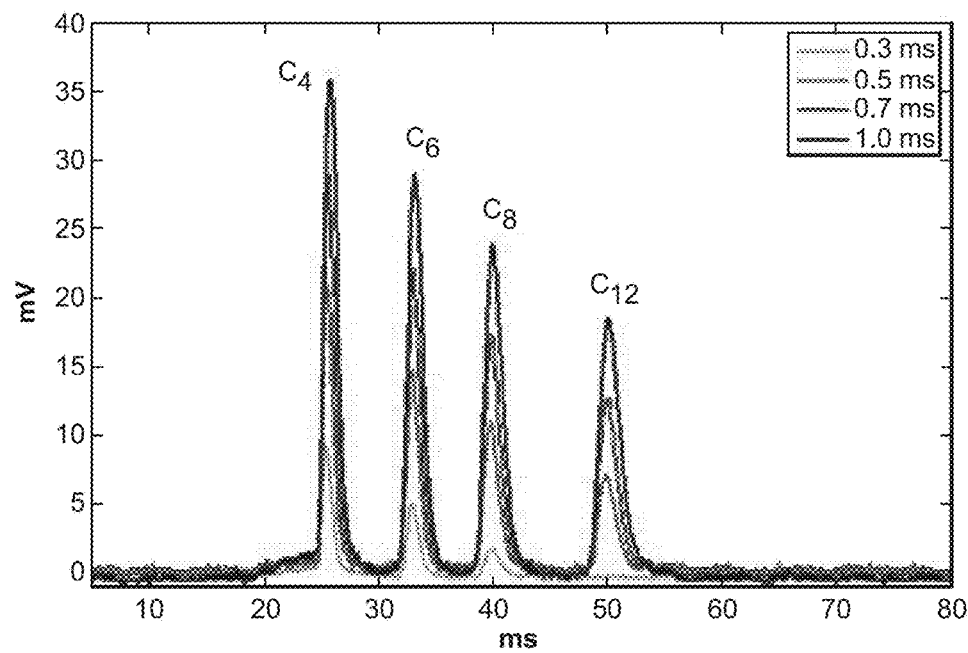
FIG. 17B shows an ion mobility spectrum of tetraalkylammonium cations separated using 3D printed IMS.

FIG. 17A shows both a mass spectrum of ions created by electrospraying a 2 mM equimolar solution of tetrabutyl-, tetrahexyl-, tertraoctyl-, and tetradodecylammonium halides in 4:1 methanol:acetonitrile with 0.1% formic acid after they are focused into an annulus by the radial ion lens, continuously injected (constant $V_{inject}$) into a drift cell, and subsequently exit the drift region where they are sampled by a mass spectrometer. A separation of ions from this same mixture was accomplished by injecting ions into the drift cell and recording their arrival times at the detection surface. FIG. 17B shows the results of this separation when injection durations ranging from 0.3 to 1.0 ms were used.

What is claimed is:

1. A system for analyzing a sample, the system comprising:
an ion generator configured to generate ions from a sample;
an ion separator comprising a plurality of electrodes that are configured to separate at or above atmospheric pressure the ions received from the ion generator; and
a detector that receives and detects the separated ions.

2. The system according to claim 1, wherein the ion generator comprises:
an ionization source; and
an ion injector configured to interface with the ionization source such that ions produced by the ionization source are received by the ion injector.

3. The system according to claim 1, wherein the ionization source is out-of-line with the detector.

4. The system according to claim 1, wherein the ion injector is maintained at or above atmospheric pressure.

5. The system according to claim 1, wherein the ion injector comprises a cavity and one or more wire meshes that receive the ions produced by the ionization source.

6. The system according to claim 1, wherein the ion injector receive the ions produced by the ionization source and transmits them as a focused beam to the ion separator.

7. The system according to claim 1, wherein the ion separator further comprises a chamber and the plurality of electrodes that are configured such that upon application of voltage to the electrodes, ions received from the ion injector are separated as they travel through the chamber.

8. The system according to claim 7, wherein the plurality of electrodes are three curved electrodes.

9. The system according to claim 8, wherein each of the three curved electrodes are separated from each other by a non-conductive spacer.

10. The system according to claim 1, wherein the detector is a mass spectrometer or a miniature mass spectrometer.

11. A method for analyzing a sample, the method comprising:
   generating ions from a sample at or above atmospheric pressure;
   separating the ions at or above atmospheric pressure in an ion separator via application of voltage to the ions from a plurality of electrodes of the ion separator as the ions travel through the ion separator; and
   detecting the separated ions, thereby analyzing the sample.

12. The method according to claim 11, wherein the detecting step is at or above atmospheric pressure.

13. The method according to claim 11, wherein the detecting step is below atmospheric pressure.

14. The method according to claim 11, wherein detecting comprises receiving the ions into a mass spectrometer or a miniature mass spectrometer.

15. The method according to claim 11, wherein the sample is derived from a mammal.

16. The method according to claim 15, wherein the sample is a mammalian tissue or body fluid sample.

17. The method according to claim 11, wherein the sample is a food or drug product.

18. The method according to claim 11, wherein the plurality of electrodes are three curved electrodes.

19. The method according to claim 18, wherein each of the three curved electrodes are separated from each other by a non-conductive spacer.

* * * * *